(12) United States Patent
Iwahori

(10) Patent No.: US 8,341,791 B2
(45) Date of Patent: Jan. 1, 2013

(54) ELECTRIC TOOTHBRUSH

(75) Inventor: Toshiyuki Iwahori, Mishima-gun (JP)

(73) Assignee: Omron Healthcare Co., Ltd., Kyoto (JP)

( * ) Notice: Subject to any disclaimer, the term of this patent is extended or adjusted under 35 U.S.C. 154(b) by 162 days.

(21) Appl. No.: 12/990,308

(22) PCT Filed: Jun. 1, 2009

(86) PCT No.: PCT/JP2009/059986
§ 371 (c)(1),
(2), (4) Date: Oct. 29, 2010

(87) PCT Pub. No.: WO2009/148018
PCT Pub. Date: Dec. 10, 2009

(65) Prior Publication Data
US 2011/0041269 A1 Feb. 24, 2011

(30) Foreign Application Priority Data

Jun. 2, 2008 (JP) ................ 2008-144161

(51) Int. Cl.
*A61C 17/22* (2006.01)

(52) U.S. Cl. .................................. 15/22.1

(58) Field of Classification Search ......... 15/22.1, 15/28
See application file for complete search history.

(56) References Cited

U.S. PATENT DOCUMENTS

| 5,749,381 | A | 5/1998 | Butler et al. | |
|---|---|---|---|---|
| 5,850,659 | A | 12/1998 | Butler et al. | |
| 6,739,012 | B2 * | 5/2004 | Grez et al. | 15/22.1 |
| 7,310,844 | B1 * | 12/2007 | Rehkemper | 15/22.1 |
| 2007/0294847 | A1 * | 12/2007 | Wang | 15/22.2 |
| 2008/0022469 | A1 * | 1/2008 | Hilscher et al. | 15/22.1 |
| 2009/0092955 | A1 | 4/2009 | Hwang | |

FOREIGN PATENT DOCUMENTS

| JP | U-58-139937 | 9/1983 |
|---|---|---|
| JP | A-2000-507464 | 6/2000 |
| JP | A-2003-9950 | 1/2003 |
| JP | A-2005-152217 | 6/2005 |
| WO | WO 2006/137648 A1 | 12/2006 |

OTHER PUBLICATIONS

International Search Report mailed Jul. 14, 2009 issued in International Patent Application No. PCT/JP2009/059986 (with translation).

* cited by examiner

*Primary Examiner* — Mark Spisich
*Assistant Examiner* — Michael Jennings
(74) *Attorney, Agent, or Firm* — Oliff & Berridge, PLC

(57) ABSTRACT

An electric toothbrush includes an electric toothbrush main body that includes a grip portion; a brush member that includes a brush; a motor that moves the brush; an actuator that relatively rotates the brush member with respect to the electric toothbrush main body in order to change an orientation of the brush; an acceleration sensor that detects an attitude of the main body; and a CPU that controls the actuator such that a brush angle becomes a predetermined optimum value based on the detected attitude.

12 Claims, 23 Drawing Sheets

[0 degrees]

[45 degrees]

[90 degrees]

First resonance:
about 12500 spm

Out of resonance:
about 26500 spm

Second resonance:
about 38000 spm

ELECTRIC TOOTHBRUSH

TECHNICAL FIELD

The present invention relates to an electric toothbrush.

BACKGROUND ART

There is well known a type of electric toothbrush in which a brush moving at high speed abut on teeth to perform brushing of teeth (remove a food residue or dental plaque). In such electric toothbrushes, an obtained cleaning effect depends on an angle at which the brush abuts on the teeth. For example, when the brush abuts on a tooth axis at 90 degrees, the highest dental plaque removing force can be exerted with respect to a tooth plane. When the brush abuts on the tooth axis at 45 degrees, a tip of brush invades easily into an interdentium or a periodontal pocket (between tooth and gum-ridge), and the food residue or the dental plaque can effectively be scraped out from the interdentium or the periodontal pocket.

Thus, there is an optimum brush angle (angle of the brush with respect to the tooth axis) according to a brushing region or the desired cleaning effect. However, few users are conscious of the desired brush angle. Even if the user is conscious of the brush angle, because the user cannot confirm a state in which the brush abuts actually on the teeth during the brushing of teeth, the brush angle is hardly matched with the optimum value.

For example, Patent Document 1 discloses an idea in which an orientation of the toothbrush main body about an axis is detected at four or eight stages to estimate the brushing region from the detection result. Specifically, a plurality of fan-like partitions are circumferentially provided in the main body, and which partition a conductive sphere is in is detected from a change in electric resistance, thereby estimating the orientation of the toothbrush main body. However, the mechanism disclosed in Patent Document 1 is hardly miniaturized and implemented.

PRIOR ART DOCUMENT

Patent Document

Patent Document 1: Japanese Unexamined Patent Publication No. 2005-152217

SUMMARY OF THE INVENTION

Problem to be Solved by the Invention

An object of the present invention is to provide a technique of realizing easily the proper brush angle in the electric toothbrush.

Means for Solving the Problem

In order to achieve the object, the present invention adopts the following configurations.

An electric toothbrush according to the present invention includes: an electric toothbrush main body that includes a grip portion; a brush member that includes a brush; driving means for moving the brush; rotation means for relatively rotating the brush member with respect to the electric toothbrush main body in order to change an orientation of the brush; attitude detection means for detecting an attitude of the electric toothbrush main body; and control means for controlling the rotation means such that a brush angle that is of an angle of the brush with respect to a tooth axis becomes a predetermined optimum value based on the detected attitude.

With this configuration, the brush member is automatically rotated according to the attitude of the electric toothbrush, and the control is performed such that the brush angle becomes the optimum value. Therefore, the proper brush angle can easily be realized during the brushing to obtain the good cleaning effect.

At this point, preferably the control means includes: region estimation means for estimating a currently-brushed brushing region in a plurality of regions defined by classifying a surface of a tooth row based on the detected attitude; and brush angle estimation means for estimating the brush angle that is of the angle of the brush with respect to the tooth axis based on the detected attitude, and the optimum value of the brush angle previously set in each brushing region and the estimated brush angle are compared to control the rotation means such that the brush angle becomes the optimum value.

Adhesion of a food residue or dental plaque depends on a kind of a tooth (such as upper jaw/lower jaw and molar tooth/cutting tooth) or a portion (such as tongue side/cheek side, a tooth surface/occluding plane, and periodontal pocket), and the effective brush angle varies in each region. Even in the same kind of the tooth, a brush applying method turns 180 degrees around on the right and left of a tooth row. Therefore, like the present invention, the brushing region is estimated, and the brush angle is appropriately controlled according to the estimation result, which allows the better cleaning effect to be realized.

Preferably the control means controls the driving means such that a motion direction or a motion frequency of the brush is changed according to the detected attitude. For example, when the driving means is formed by a rotary motor, a rotating direction of the rotary motor is switched or the number of rotations is changed, which allows a motion direction or a motion frequency of the brush to be changed.

Thus, the better cleaning effect can be realized by controlling not only the brush angle but also the motion of the brush.

Preferably the attitude detection means detects the attitude based on an output of an acceleration sensor.

Therefore, the attitude can be determined with high accuracy, and the brushing region and the brush angle can be estimated with high accuracy and high resolution than ever before. Because the acceleration sensor is compact, the acceleration sensor can easily be assembled in the electric toothbrush main body. A uniaxial acceleration sensor can be used, and preferably multiaxis (biaxial, triaxial, or more) acceleration sensor can be used.

Preferably the electric toothbrush further includes informing means for informing that the brush angle is the optimum value. Therefore, usability can be improved. For example, light, sound, voice, and vibration can be used as the informing method.

Preferably the optimum value can be changed. Therefore, the electric toothbrush can flexibly be used such that the brush angle is set to 90 degrees when it is desired to obtain the high dental plaque removing force, and such that the brush angle is set to 45 degrees when it is desired to effectively brush a region such as the periodontal pocket between the tooth and the gum-ridge.

Preferably the control means controls the rotation means such that the brush member is located at a predetermined initial position after the electric toothbrush is used or when use of the electric toothbrush is started. Therefore, even if the brushing of teeth is ended while the orientation of the brush is deviated from the initial position, the orientation of the brush is automatically returned to the initial position until the next brushing of teeth is started. Therefore, the optimum brush angle can quickly be realized when the brushing of teeth is started.

The means and the pieces of processing are combined as much as possible to be able to made the present invention.

Effect of the Invention

According to the present invention, the proper brush angle can easily be realized in the electric toothbrush.

BEST MODES FOR CARRYING OUT THE INVENTION

Preferred embodiments of the present invention will be described in detail below with reference to the drawings.

First Embodiment

Configuration of Electric Toothbrush

Figure 1:
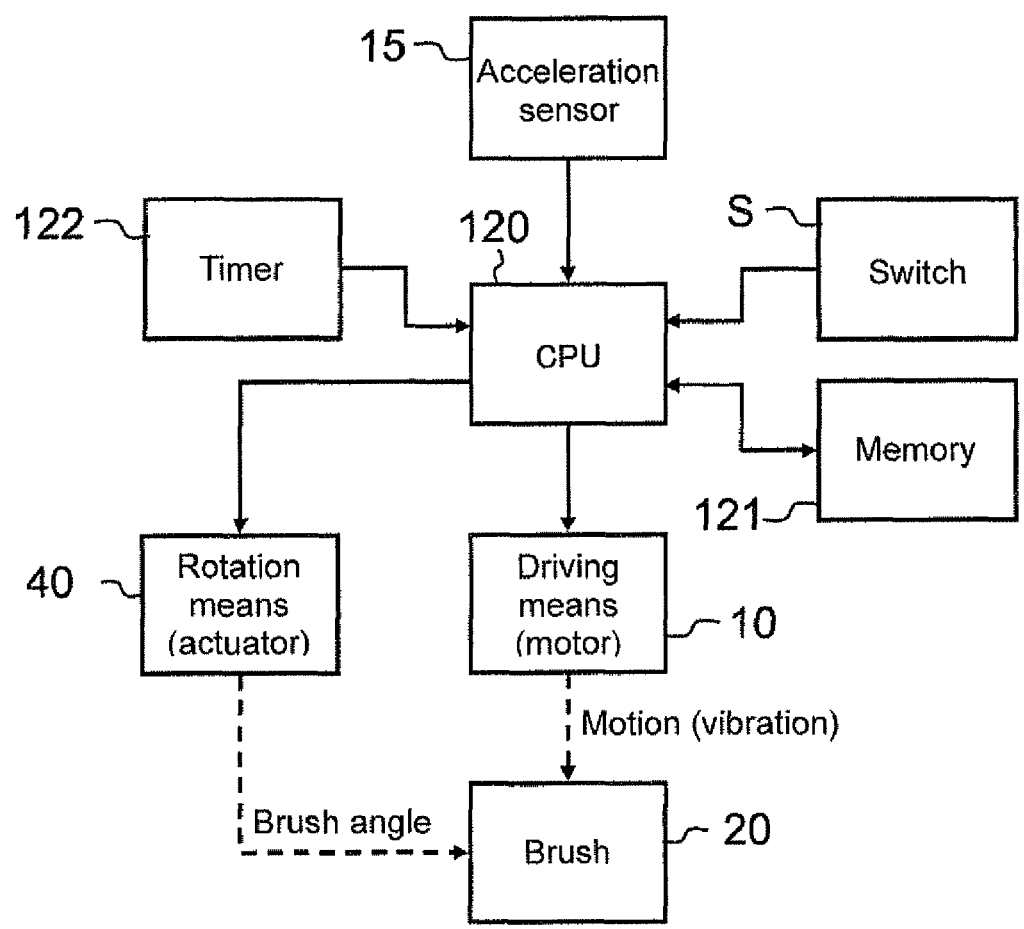
FIG. 1 is a block diagram of an electric toothbrush according to a first embodiment.
Figure 2:
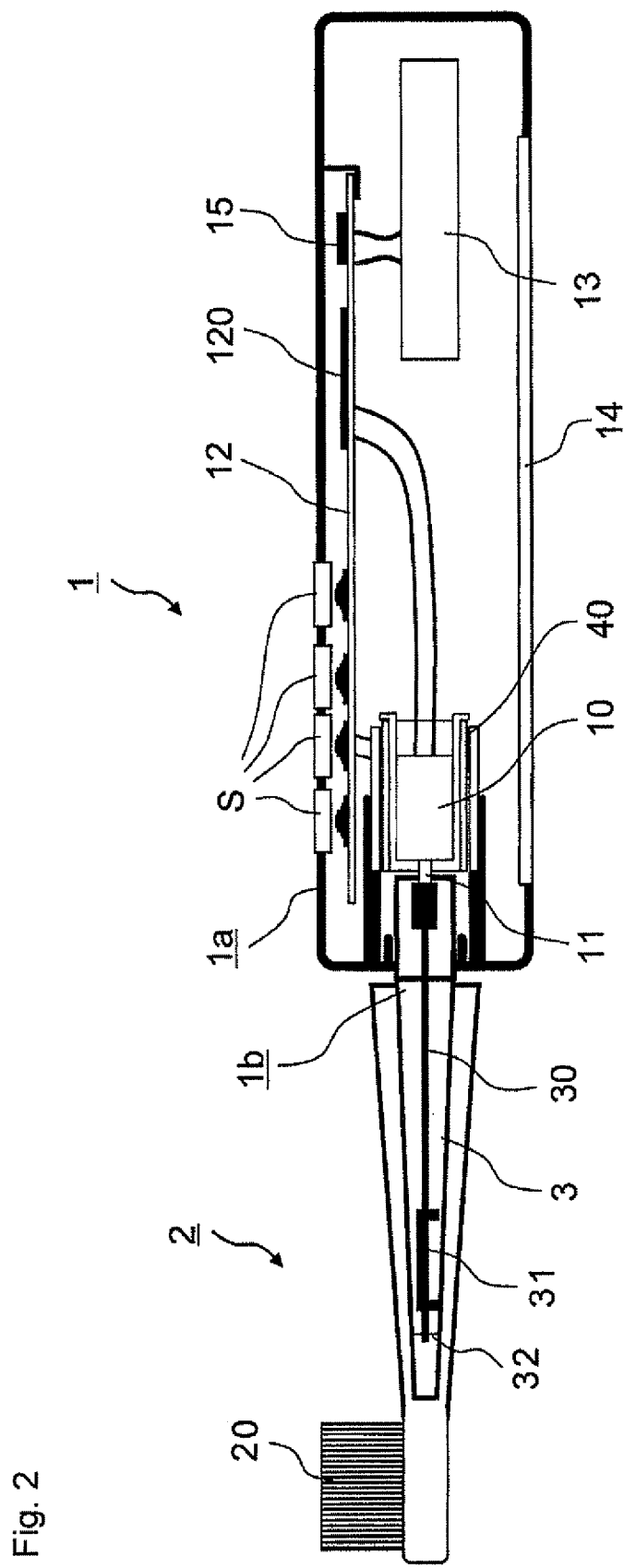
FIG. 2 is a sectional view illustrating an internal configuration of the electric toothbrush of the first embodiment.
Figure 3:
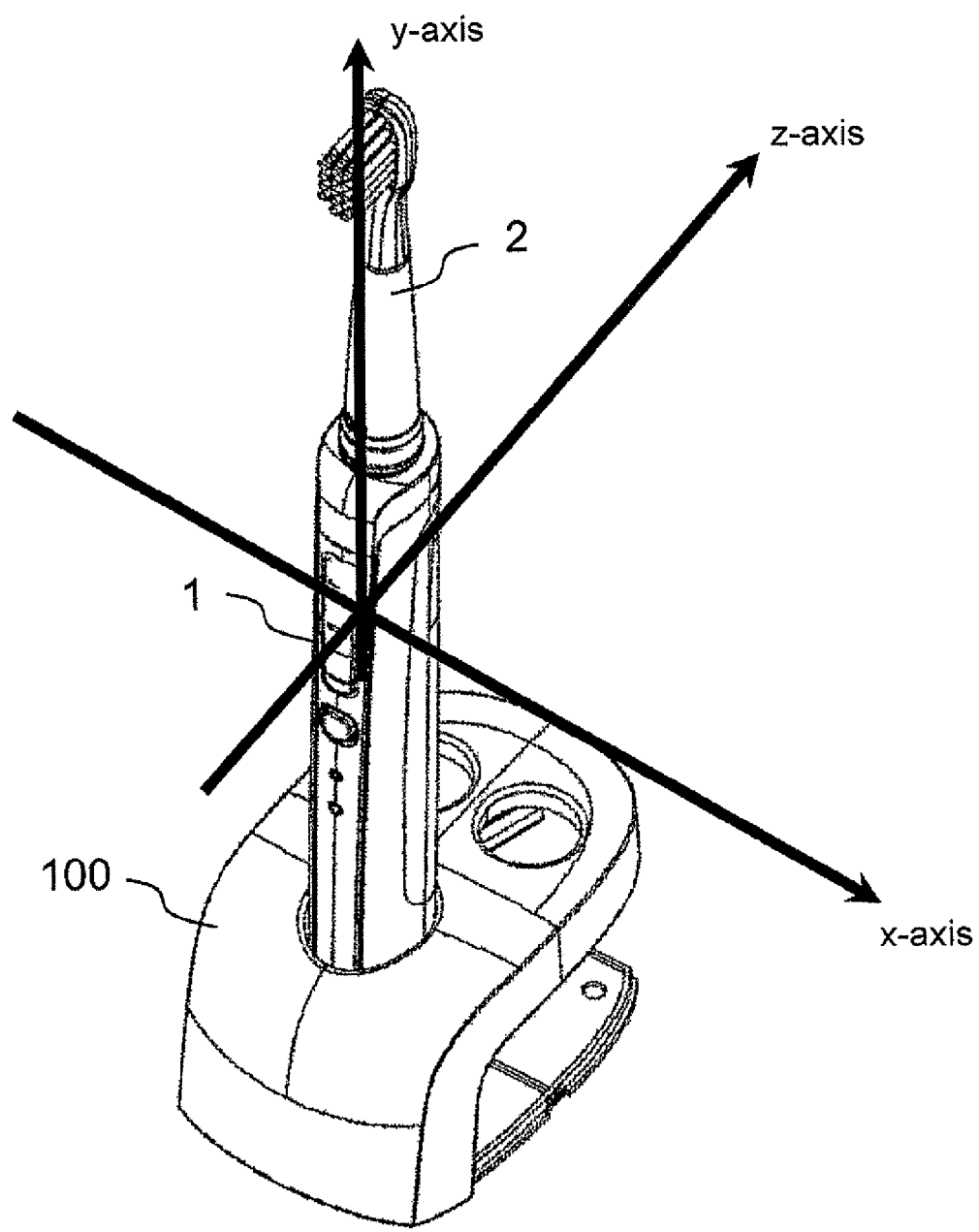
FIG. 3 is a perspective view illustrating an appearance of the electric toothbrush.

A configuration of an electric toothbrush will be described with reference to FIGS. 1, 2, and 3. FIG. 1 is a block diagram of the electric toothbrush of the first embodiment, FIG. 2 is a sectional view illustrating an internal configuration of the electric toothbrush of the first embodiment, and FIG. 3 is a perspective view illustrating an appearance of the electric toothbrush.

The electric toothbrush includes an electric toothbrush main body 1 (hereinafter simply referred to as the "main body 1") and a brush member 2. The main body 1 includes an outer chassis 1$a$ and an inner chassis 1$b$. The brush member 2 is attached to the inner chassis 1$b$ of the main body 1.

The outer chassis 1$a$ of the main body 1 is formed by a resin case having a substantially cylindrical shape. An elastomer grip portion 14 and a switch S are provided in the outer chassis 1$a$. The grip portion 14 is held with a hand of a user in brushing the teeth. The switch S is used in power-on and -off and mode switching.

A motor 10 that is of a driving source, a driving circuit 12, a rechargeable battery 13 that is of a 2.4V-power supply, a recharging coil (not illustrated) and the like are provided in the outer chassis 1$a$ of the main body 1. In recharging the rechargeable battery 13, only the main body 1 is placed on a charger 100 to be able to recharge the rechargeable battery 13 in a non-contact manner by electromagnetic induction. The driving circuit 12 includes a CPU (input/output processing unit) 120 that performs various kinds of operation/control, a memory 121 that stores a program and various setting values, a timer 122 and the like.

(Acceleration Sensor)

An acceleration sensor 15 is provided in the main body 1. A multiaxis acceleration sensor may be used as the acceleration sensor 15, or a uniaxial acceleration sensor may be used as the acceleration sensor 15. The triaxial acceleration sensor is placed, as illustrated in FIG. 3, such that an x-axis becomes parallel to a brush surface, such that a y-axis is matched with a longitudinal direction of the main body 1, and such that a z-axis is perpendicular to the brush surface. As used herein, "brush surface" means a virtual plane that is substantially orthogonal to bristles (fiber) of the brush and located at leading end portions of the bristles. For the uniaxial acceleration sensor, the acceleration sensor may be placed so as to detect acceleration in a z-axis direction or an x-axis direction of FIG. 3. In the first embodiment, the x, y, and z triaxial acceleration sensor is used. An output of the acceleration sensor 15 is inputted to the CPU 120 and used to detect a three-dimensional attitude of the brush.

Piezoelectric resistance type, electrostatic capacitance type, or heat sensing type MEMS sensors can preferably be used as the acceleration sensor 15. This is because the extremely compact MEMS sensor is easily assembled in the main body 1. However, the acceleration sensor 15 is not limited to the MEMS sensor. For example, electric motor type, strain gage type, and piezoelectric type sensors may be used as the acceleration sensor 15. Although not illustrated, a correction circuit may be provided in order to correct a sensitivity balance of sensors of the axes, a temperature characteristic of sensitivity, and a temperature drift. A bandpass filter (lowpass filter) may be provided in order to remove a dynamic acceleration component or a noise. The noise may be reduced by smoothing an output waveform of the acceleration sensor.

(Driving Mechanism of Brush)

The inner chassis 1b of the main body 1 is a component that is attached to the outer chassis 1a while being relatively movable. The inner chassis 1b includes a stem 3 that is provided so as to be protruded from an opening of a leading end side (brush side) of the outer chassis 1a. The brush member 2 is mounted such that the stem 3 is covered therewith. A brush 20 is implanted at a leading end of the brush member 2. Because the brush member 2 is consumable goods, the brush member 2 is configured to de detachably attached to the stem 3 (inner chassis 1b) so as to be replaced with new one.

The stem 3 made of a resin material is formed into a tubular shape whose distal end (an end portion on the brush side) is closed, and the stem 3 includes a bearing 32 at the distal end in the tube. A distal end of an eccentric shaft 30 coupled to a rotating shaft 11 of the motor 10 is inserted in the bearing 32 of the stem 3. The eccentric shaft 30 includes a weight 31 near the bearing 32, and a gravity center of the eccentric shaft 30 is deviated from a rotation center of the eccentric shaft 30. When the CPU 120 supplies a driving signal (for example, a pulse width modulation signal) to the motor 10 according to an operation mode to rotate the rotating shaft 11 of the motor 10, the eccentric shaft 30 is also rotated in association with the rotation of the rotating shaft 11, and the eccentric shaft 30 gyrates around the rotation center because the gravity center of the eccentric shaft 30 is deviated. Therefore, the distal end of the eccentric shaft 30 collides repeatedly slightly with an inner wall of the bearing 32 to vibrate (move) the brush 20 at high speed. That is, the motor 10 acts as driving means for vibrating (moving) the brush, and the eccentric shaft 30 acts as a motion transmission mechanism (motion conversion mechanism) that converts the output (rotation) of the motor 10 into the vibration of the brush 20.

(Rotating Mechanism of Brush Member)

Figure 4:
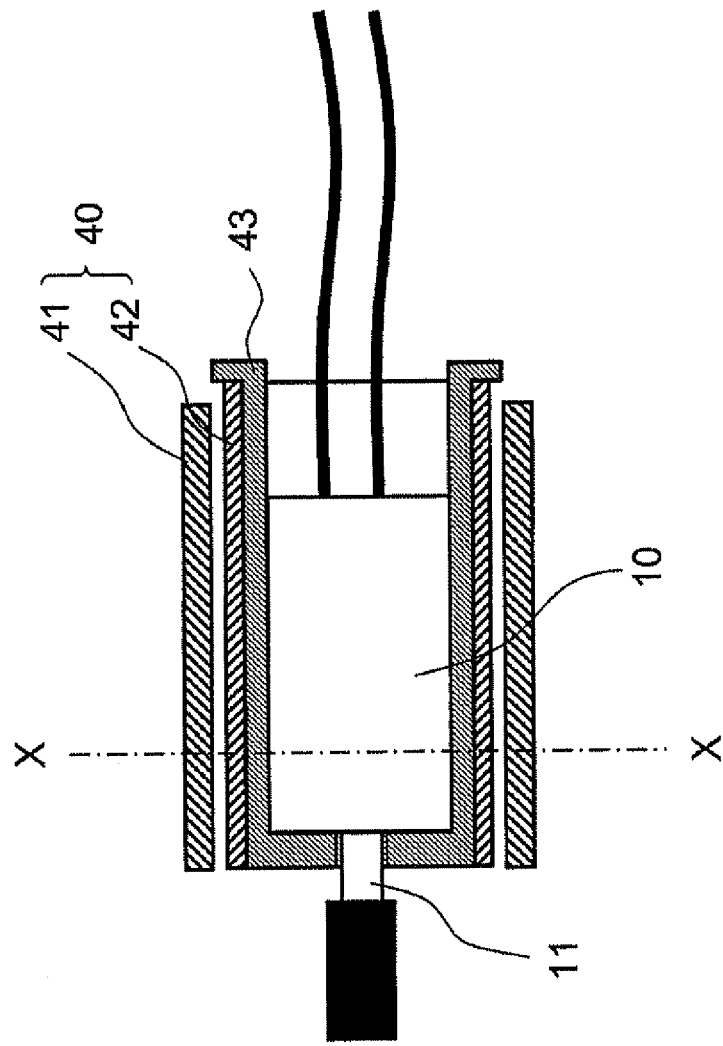
FIGS. 4A and 4B are views each illustrating a configuration of a brush angle controlling actuator.
Figure 4:
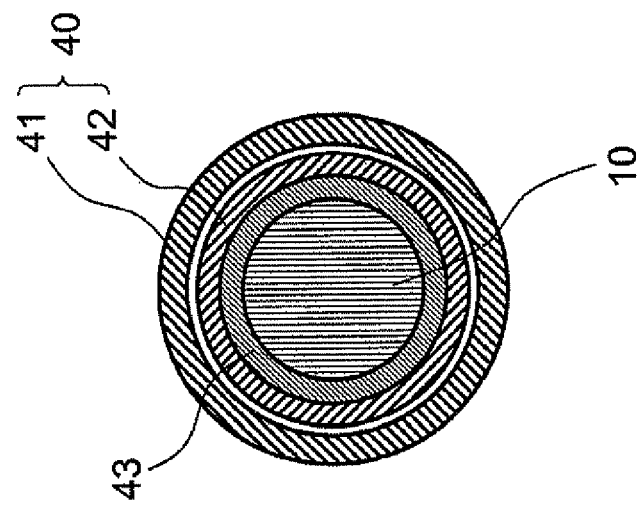

The electric toothbrush of the first embodiment includes an actuator (rotation means) 40 for relatively rotating the brush member 2 with respect to the outer chassis 1a of the main body 1 in order to change an orientation of the brush 20 about the y-axis. FIGS. 4A and 4B illustrate a configuration of the actuator 40. FIG. 4A is a sectional view taken on line X-X of FIG. 4B.

The actuator 40 is formed by a rotary type motor that includes a stator 41 and a rotor 42. The stator 41 is fixed to the outer chassis 1a of the main body 1, and the rotor 42 is fixed to a motor housing 43 of the motor 10. When the control signal is supplied from the CPU 120 to the actuator 40, the rotor 42 is rotated by an angle according to the control signal. In the first embodiment, it is assumed that a rotation angle of the rotor 42 ranges from −180 degrees to +180 degrees. The motor housing 43 and the motor 10 are rotated in association with the rotation of the rotor 42, and the inner chassis 1b fixed to the rotating shaft 11 of the motor 10 is also rotated. As a result, the brush member 2 is rotated by a desired angle with respect to the main body 1, which allows the orientation of the brush 20 to be changed. As used herein, "orientation of brush" means a direction normal to the brush surface, that is, a direction of a tip of the brush, and "change orientation of brush" means that the rotation angle about the y-axis of the orientation of the brush is changed.

A well-known rotary type motor such as a stepping motor can preferably used as the actuator 40. For example, a cylindrical type linear motor including an arc stator can be used as the actuator 40 because it is only necessary to obtain the rotation output.

As described above, the electric toothbrush of the first embodiment includes the two kinds of the actuators, that is, the motor 10 that moves (vibrates) the brush 20 and the actuator 40 that controls the orientation (brush angle) of the brush 20. In order to distinguish from each other, the motor 10 may be referred to as a brush driving actuator, and the actuator 40 may be referred to as a brush angle controlling actuator.

(Operation of Electric Toothbrush)

Adhesion of a food residue or dental plaque depends on a kind of a tooth (such as upper jaw/lower jaw and molar tooth/cutting tooth) or a portion (such as tongue side/cheek side, a tooth surface/occluding plane, and periodontal pocket), and the effective brush angle varies in each region. Even in the same kind of the tooth, a brush applying method turns 180 degrees around on the right and left of a tooth row.

Therefore, in the electric toothbrush of the first embodiment, the brushing region is estimated based on the brush attitude detected by the acceleration sensor 15, and the actuator 40 is controlled such that the brush angle becomes optimum according to the brushing region.

Figure 5:
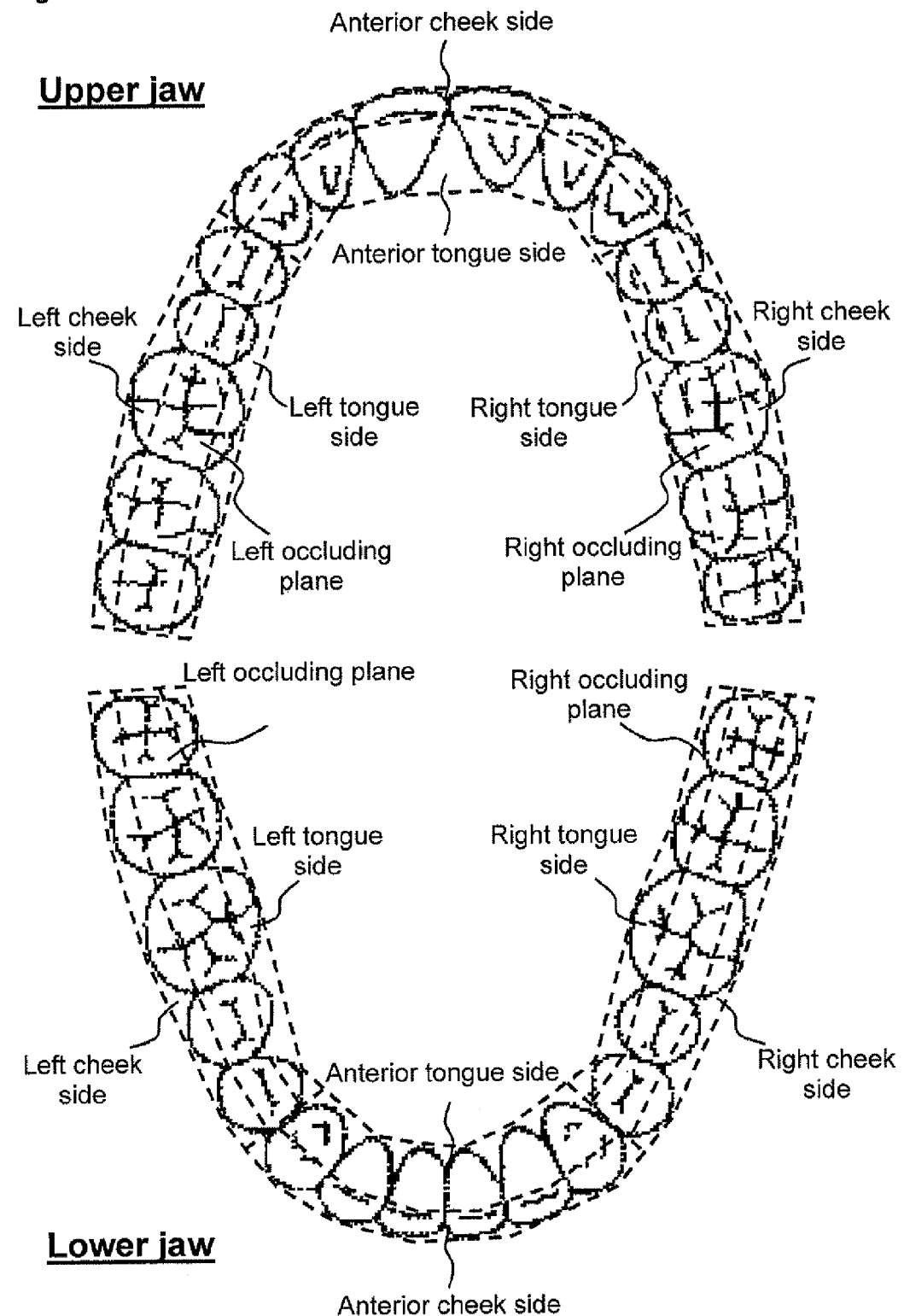
FIG. 5 is a view illustrating segmentation of a brushing region.

In the first embodiment, as illustrated in FIG. 5, the upper and lower tooth rows are classified into 16 regions, that is, "upper jaw anterior cheek side", "upper jaw anterior tongue side", "upper jaw left cheek side", "upper jaw left tongue side", "upper jaw left occluding plane side", "upper jaw right cheek side", "upper jaw right tongue side", "upper jaw right occluding plane side", "lower jaw anterior cheek side", "lower jaw anterior tongue side", "lower jaw left cheek side", "lower jaw left tongue side", "lower jaw left occluding plane side", "lower jaw right cheek side", "lower jaw right tongue side", and "lower jaw right occluding plane side". However, the classification of the tooth row is not limited to the first embodiment. The tooth row may be more broadly classified, or the tooth row may be more finely classified.

Figure 6:
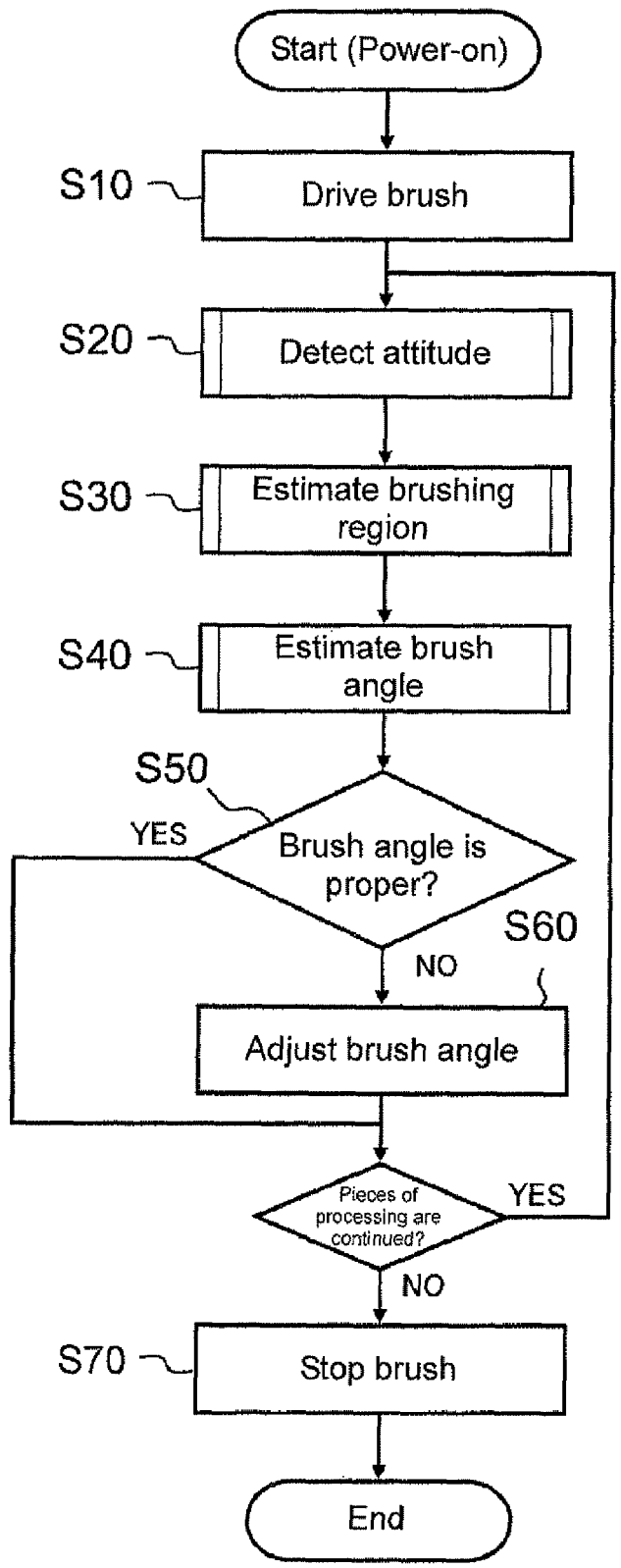
FIG. 6 is a flowchart illustrating a main routine of an operation of the electric toothbrush.
Figure 7:
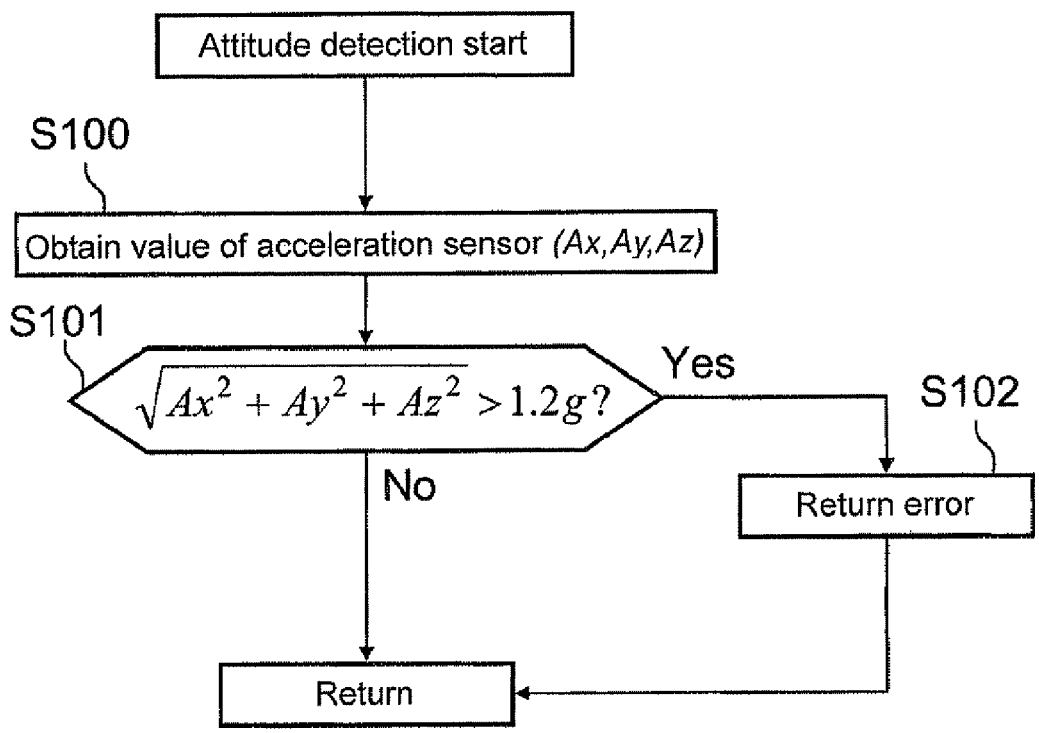
FIG. 7 is a flowchart of attitude detecting processing.
Figure 8:
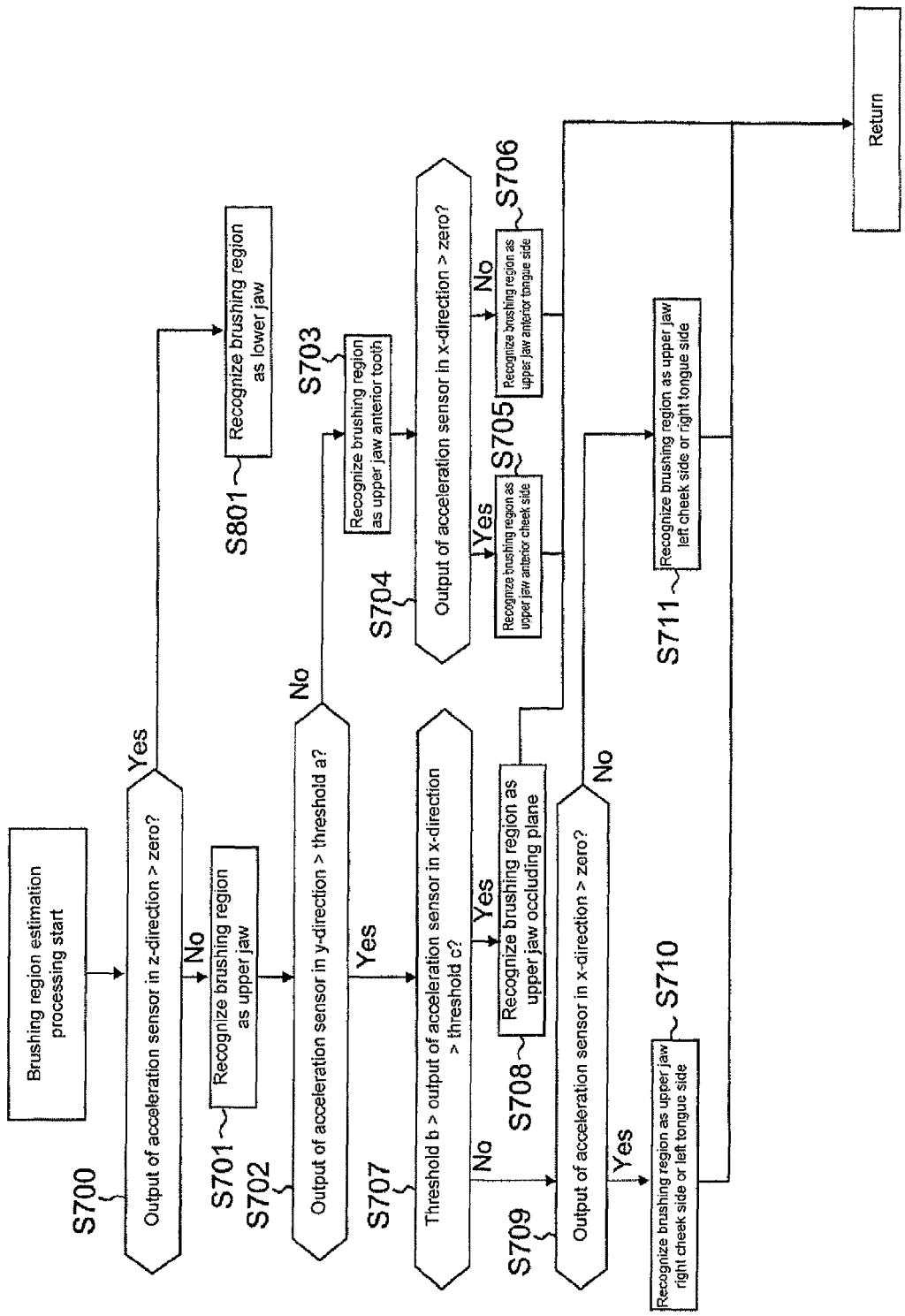
FIG. 8 is a flowchart of brushing region estimating processing (upper jaw).
Figure 9:
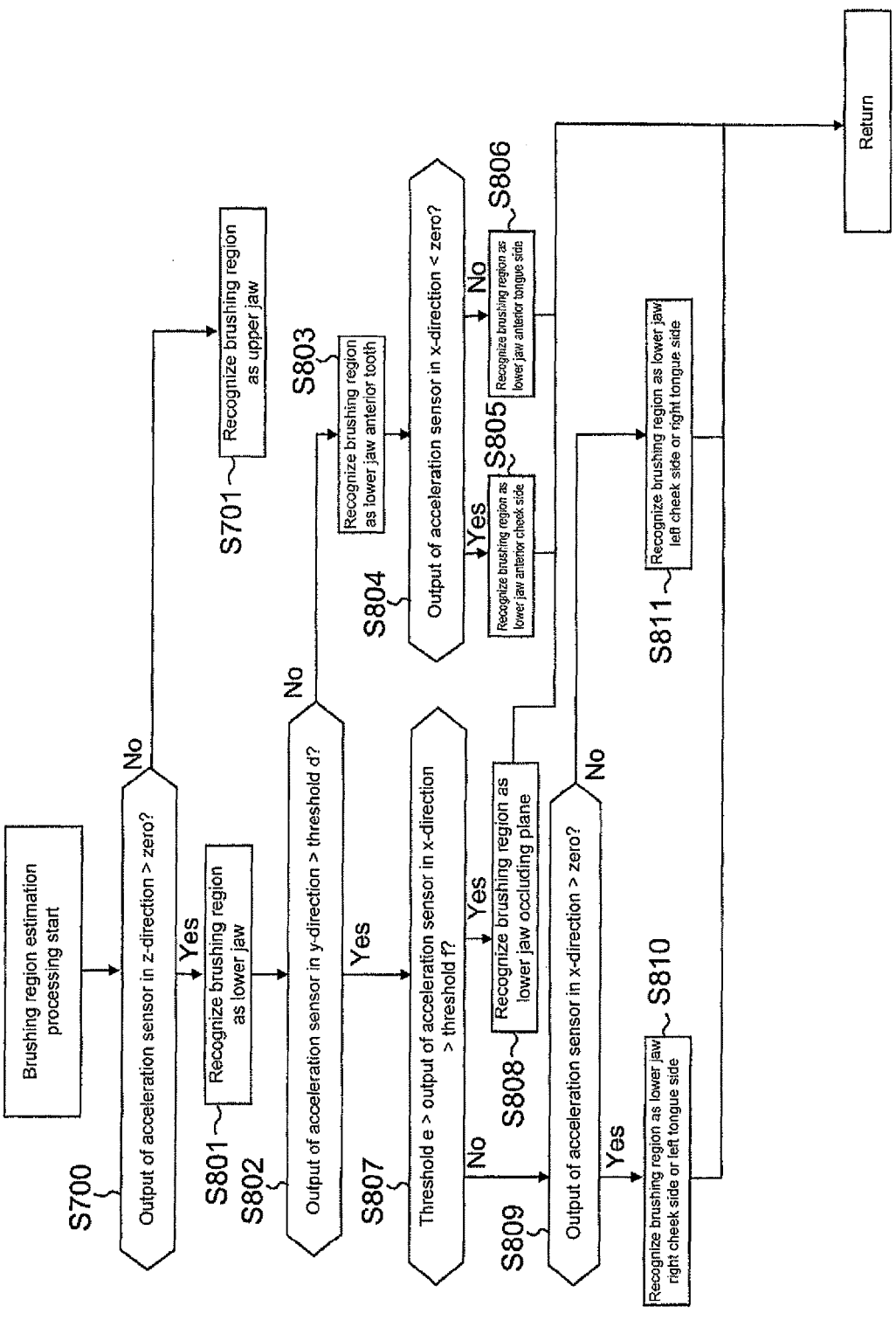
FIG. 9 is a flowchart of brushing region estimating processing (lower jaw).

An automatic control flow of the brush angle will specifically be described with reference to flowcharts of FIGS. 6 to 9. FIG. 6 is a flowchart of a main routine, and FIGS. 7 to 9 are flowcharts illustrating detailed pieces of processing of the main routine. The CPU 120 that is of the control means performs the following pieces of processing according to a program unless otherwise noted.

When the electric toothbrush is powered on, the CPU 120 controls the motor 10 to start the drive of the brush 20 (S10). The following pieces of processing in S20 to S60 are repeatedly performed at constant time intervals. Then the electric toothbrush is powered off, or when a continuous operation time measured by a timer reaches a predetermined time (for example, two minutes), a loop of S20 to S60 is ended (pieces of processing are continued?: NO), and the CPU 120 stops the drive of the brush 20 (S70).

(S20: Attitude Detection)

In S20, the CPU 120 detects the attitude of the electric toothbrush main body based on the output of the acceleration sensor 15. FIG. 7 is a flowchart of attitude detecting processing (S20).

The CPU 120 obtains outputs Ax, Ay, Az of x, y, z from the acceleration sensor 15 (S100). Ax expresses an acceleration component of an x-direction, Ay expresses an acceleration component of a y-direction, and Az expresses an acceleration component of a z-direction. When the toothbrush is in a resting state (when dynamic acceleration does not act on the acceleration sensor 15), a resultant vector A of Ax, Ay, Az corresponds to gravitational acceleration. At this point, A=(Ax, Ay, Az) is referred to as an attitude vector.

When magnitude of the attitude vector A=(Ax, Ay, Az) is more than 1.2 g (g is the gravitational acceleration) (YES in S101), an error is returned (S102). This is because the correct direction of the gravitational acceleration (that is, three-dimensional attitude of brush) is hardly specified when a large amount of dynamic acceleration components are included in the acceleration sensor output. Alternatively, the error is not returned unlike S102, but the pieces of processing S100 and S101 may be repeated until the acceleration sensor outputs Ax, Ay, Az whose magnitude of the resultant vector is 1.2 g or less are obtained. A threshold value for the error determination is not limited to 1.2 g, but another value may be made.

(S30: Estimation of Brushing Region)

Figure 10:
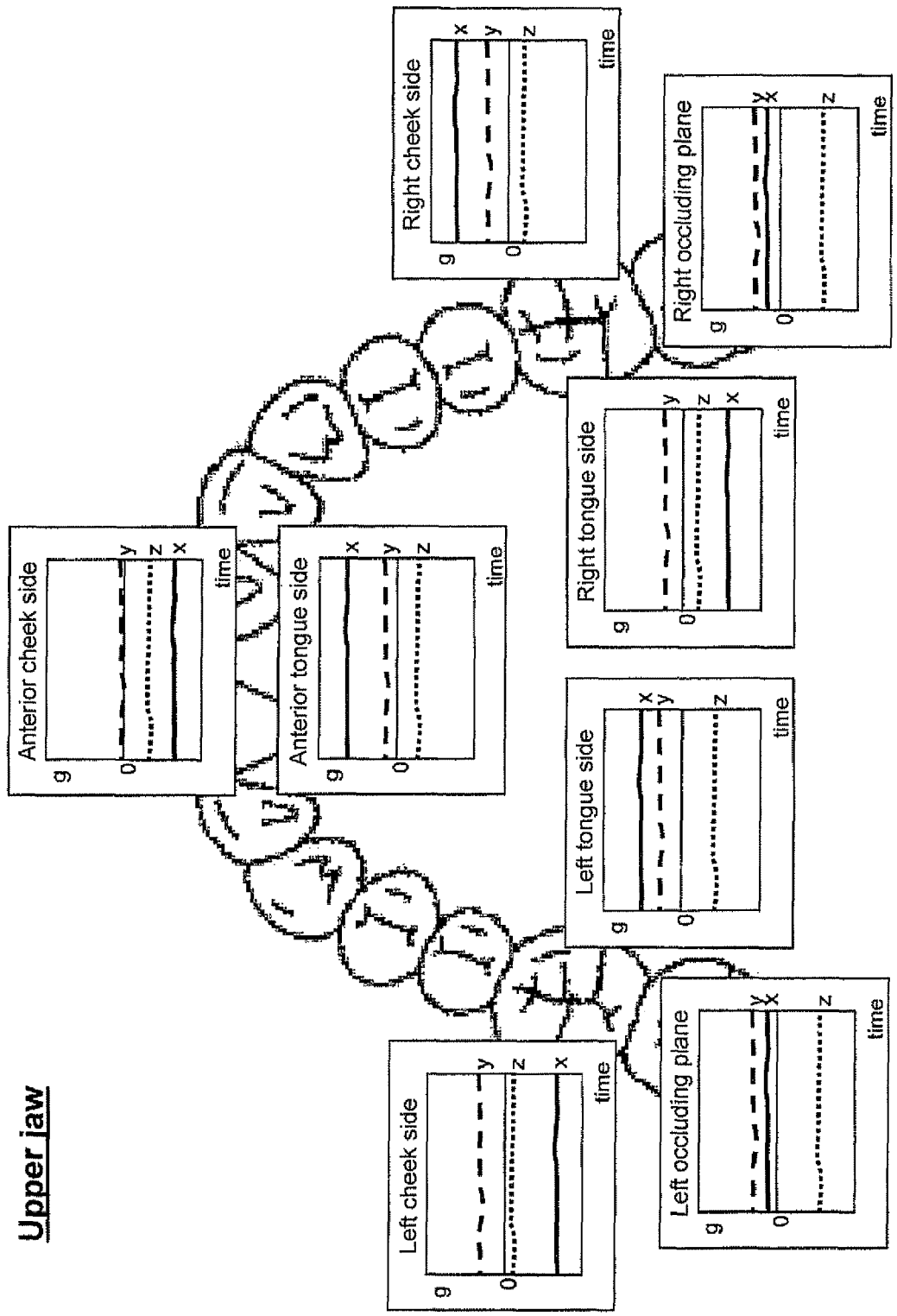
FIG. 10 is a view illustrating examples of acceleration sensor outputs Ax, Ay, Az in each brushing region of the upper jaw.
Figure 11:
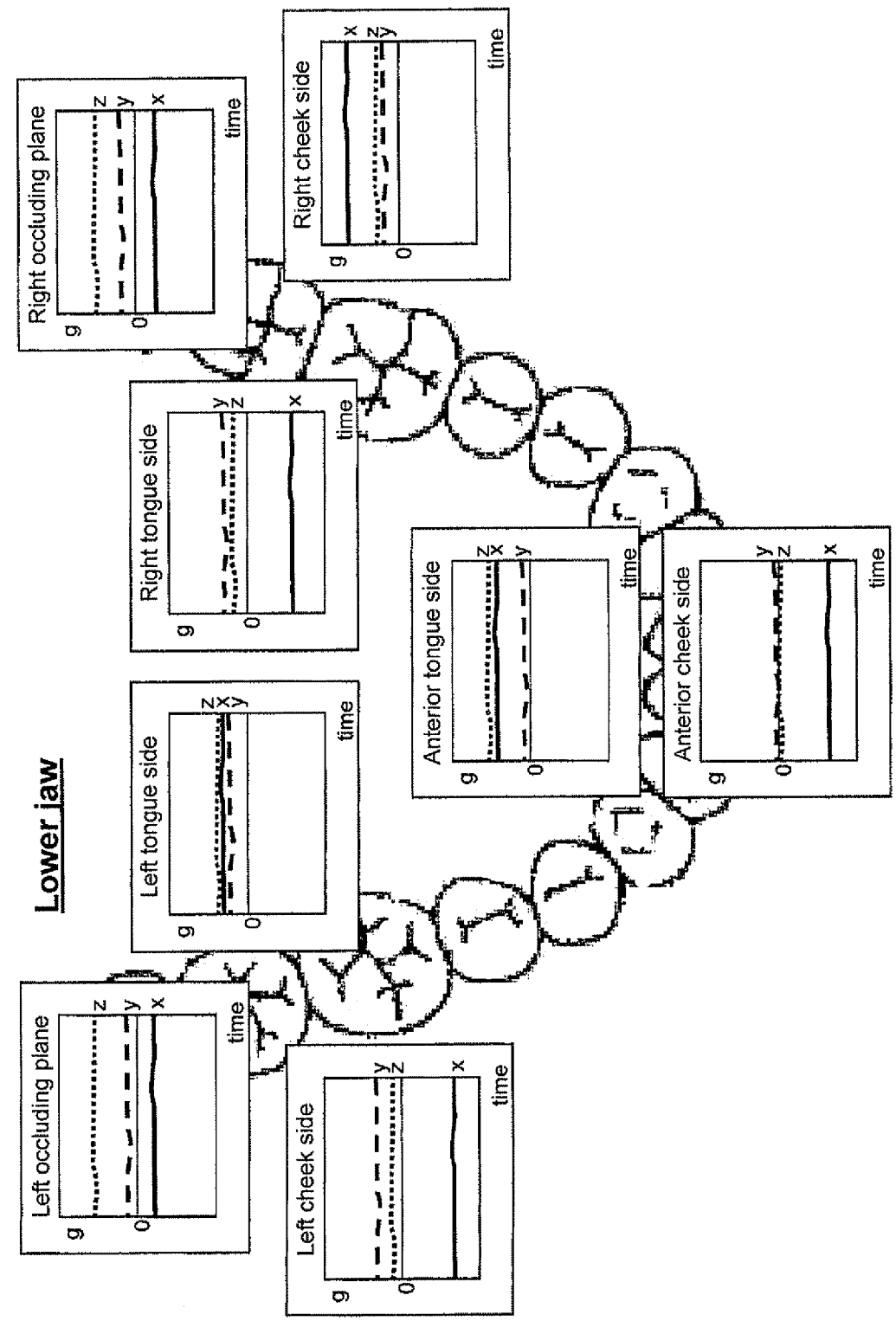
FIG. 11 is a view illustrating examples of acceleration sensor outputs Ax, Ay, Az in each brushing region of the lower jaw.

FIGS. 8 and 9 are flowcharts of brushing region estimating processing (S30). FIGS. 10 and 11 are views illustrating examples of acceleration sensor outputs Ax, Ay, Az in each brushing region.

The CPU 120 determines whether the brushing region is the upper jaw or the lower jaw based on the acceleration sensor output Az in the z-direction (S700). The determination is made based on the fact that the brush surface is considerably oriented upward when the tooth row of the upper jaw is brushed while the brush surface is considerably oriented downward when the tooth row of the lower jaw is brushed. The determination that the brushing region is the lower jaw is made for Az>0 (S801), and the determination that the brushing region is the upper jaw is made for Az≦0 (S701).

(1) For Upper Jaw

The CPU 120 determines whether the brushing region is the anterior tooth based on the acceleration sensor output Ay in the y-direction (S702). The determination is made based on the fact that the toothbrush main body 1 becomes relatively horizontal when the anterior tooth is brushed while the toothbrush main body 1 becomes necessarily oblique because of interference with a lip when the molar tooth is brushed. The determination that the brushing region is the upper jaw anterior tooth is made for Ay≦threshold a (S703).

When determining that the brushing region is the upper jaw anterior tooth, the CPU 120 determines whether the brushing region is the cheek side or the tongue side based on the acceleration sensor output Ax in the x-direction (S704). The determination is made based on the fact that the orientation of the brush is inverted by the cheek side or the tongue side. The determination that the brushing region is the "upper jaw anterior cheek side" is made for Ax>0 (S705), and the determination that the brushing region is the "upper jaw anterior tongue side" is made for Ax≦0 (S706).

On the other hand, when the brushing region is not the upper jaw anterior tooth in S702, the CPU 120 determines whether the brushing region is the occluding plane based on the acceleration sensor output Ax in the x-direction (S707). The determination is made based on the fact that the brush surface becomes substantially horizontal to extremely decrease the output of Ax when the occluding plane is brushed. The determination that the brushing region is the "upper jaw left occluding plane or upper jaw right occluding plane" is made for threshold b>Ax>threshold c (S708). In the first embodiment, the upper jaw left occluding plane and the upper jaw right occluding plane are not particularly distinguished from each other. This is because the necessity to change the brushing operation on the right and left is small for the occluding plane.

For Ax≧threshold b or Ax≦5 threshold c, the CPU 120 determines whether the brushing region is the cheek side or the tongue side based on whether Ax is larger than 0 (S709). The determination is made based on the fact that the orientation of the brush is inverted by the cheek side or the tongue side. The determination that the brushing region is the "upper jaw right cheek side or upper jaw left tongue side" is made for Ax>0 (S710), and the determination that the brushing region is the "upper jaw left cheek side or upper jaw right tongue side" is made for Ax≦0 (S711). In the first embodiment, the upper jaw right cheek side and the upper jaw left tongue side are not particularly distinguished from each other. This is because the necessity to change the brush angle and the like is small among the upper jaw right cheek region and the upper jaw left tongue region. The same holds true for the upper jaw left cheek side and the upper jaw right tongue side.

(2) For Lower Jaw

The CPU 120 determines whether the brushing region is the anterior tooth based on the acceleration sensor output Ay in the y-direction (S802). The determination is made based on the fact that the toothbrush main body 1 becomes relatively horizontal when the anterior tooth is brushed while the toothbrush main body 1 becomes necessarily oblique because of interference with a lip when the molar tooth is brushed. The determination that the brushing region is the lower jaw anterior tooth is made for Ay≦threshold d (S803).

When determining that the brushing region is the lower jaw anterior tooth, the CPU 120 determines whether the brushing region is the cheek side or the tongue side based on the acceleration sensor output Ax in the x-direction (S804). The determination is made based on the fact that the orientation of the brush is inverted by the cheek side or the tongue side. The determination that the brushing region is the "lower jaw anterior cheek side" is made for Ax<(5805), and the determination that the brushing region is the "lower jaw anterior tongue side" is made for Ax≧0 (S806).

On the other hand, when determining that the brushing region is not the lower jaw anterior tooth in S802, the CPU 120 determines whether the brushing region is the occluding plane based on the acceleration sensor output Ax in the x-direction (S807). The determination is made based on the fact that the brush surface becomes substantially horizontal to extremely decrease the output of Ax when the occluding plane is brushed, The determination that the brushing region is the "lower jaw left occluding plane or lower jaw right occluding plane" is made for threshold e>Ax>threshold f (S808). In the first embodiment, the lower jaw left occluding plane and the lower jaw right occluding plane are not particularly distinguished from each other. This is because the necessity to change the brushing operation on the right and left is small for the occluding plane.

For Ax≧threshold e or Ax≦threshold f, the CPU 120 determines whether the brushing region is the cheek side or the tongue side based on whether Ax is larger than 0 (S809). The determination is made based on the fact that the orientation of the brush is inverted by the cheek side or the tongue side. The determination that the brushing region is the "lower jaw right cheek side or lower jaw left tongue side" is made for Ax>0 (S810), and the determination that the brushing region is the "lower jaw left cheek side or lower jaw right tongue side" is made for Ax≦0 (S811). In the first embodiment, the lower jaw right cheek side and the lower jaw left tongue side are not particularly distinguished from each other. This is because the necessity to change the brush angle and the like is small among the lower jaw right cheek region and the lower jaw left tongue region. The same holds true for the lower jaw left cheek side and the lower jaw right tongue side.

Through the above-described pieces of processing, the current brushing region is specified as one of the "upper jaw anterior cheek side" (S705), the "upper jaw anterior tongue side" (S706), the "upper jaw occluding plane" (S708), the "upper jaw right cheek side or upper jaw left tongue side"

(S710), the "upper jaw left cheek side or upper jaw right tongue side" (S711), the "lower jaw anterior cheek side" (S805), the "lower jaw anterior tongue side" (S806), the "lower jaw occluding plane" (S808), the "lower jaw right cheek side or lower jaw left tongue side" (S810), and the "lower jaw left cheek side or lower jaw right tongue side" (S811).

Figure 12:
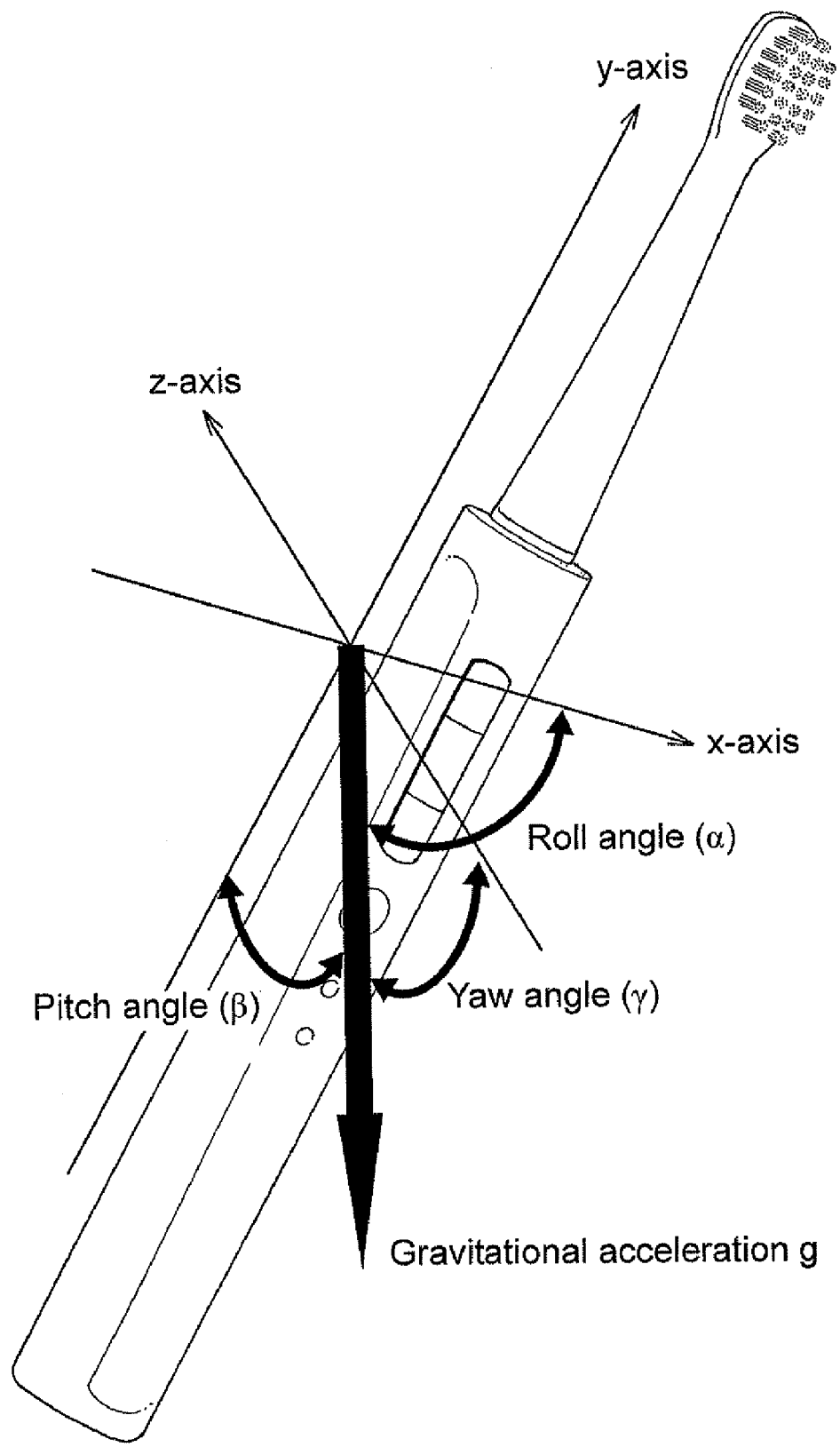
FIG. 12 is a view illustrating a definition of an attitude angle of the electric toothbrush.

The above-described determination algorithm is described only by way of example. Any determination algorithm may be used as long as the brushing region can be specified from the acceleration sensor outputs Ax, Ay, Az. For example, the values Ax, Ay, Az are not directly used as a determination variable, but a second-order variable obtained by appropriately combining Ax, Ay, Az may be used in the determination. For example, Ay/Az, Ax·Ax+A·Ay, and Az-Ax can arbitrarily set as the second-order variable. Alternatively, the determination of the brushing region may be made after pieces of acceleration information Ax, Ay, Az of the axes are converted into pieces of angle information (attitude angle) α, β, γ as illustrated in FIG. 12. In an example of FIG. 12, an angle of the x-axis with respect to the direction of the gravitational acceleration is defined as a roll angle α, an angle of the y-axis with respect to the direction of the gravitational acceleration is defined as a pitch angle β, and an angle of the z-axis with respect to the direction of the gravitational acceleration is defined as a yaw angle γ. The threshold used in the determination can be fixed from results of clinical experiments.

(S40 to S60: Control of Brush Angle)

In S40, the CPU 120 estimates a current value of the brush angle based on the attitude (acceleration sensor output) detected in S200. The brush angle is an angle at which the brush abuts on a tooth axis (axis along a head and a root of the tooth). However, in the estimation processing in S40, the brush angle is computed on the assumption that the rotation angle of the inner chassis 1b is 0 degrees by the actuator 40 while the tooth axis is matched with the gravitation direction. At this point, it is assumed that the brush angle expressed in the range of 0 degrees to 90 degrees.

Figure 13:
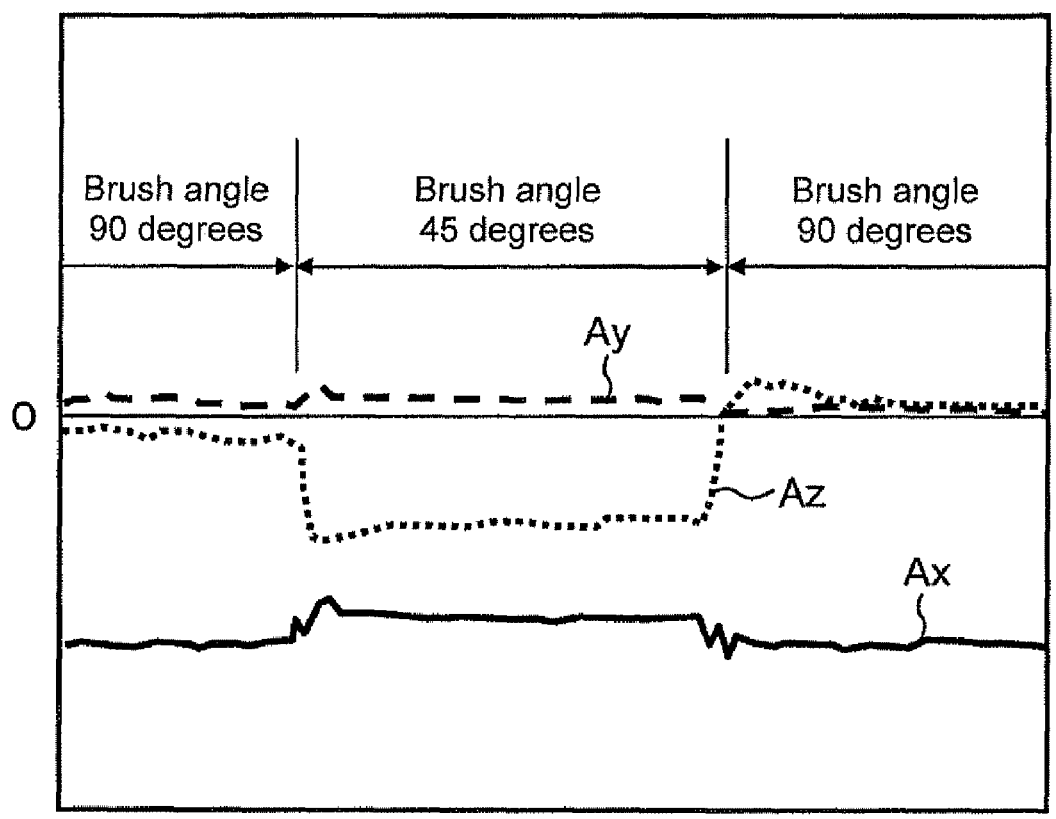
FIG. 13 is a view illustrating a waveform change of a sensor output according to a change in brush angle.

For example, the brush angle can be estimated from the acceleration component Az in the z-direction. As illustrated in FIG. 13, the value Az is significantly changed according to the brush angle such that Az substantially exhibits 0 when the brush angle is about 90 degrees, and such that the value of Az is increased with decreasing brush angle. Because the acceleration component Ax in the x-direction is also changed according to the brush angle, preferably the brush angle is estimated from Ax instead of Az or the brush angle is estimated from both Ax and Az (the direction of the resultant vector of Ax and Az). The brush angle may be computed as a continuous amount, or the brush angle may be computed as a discrete value such as 0 degrees to 10 degrees and 10 degrees to 20 degrees.

Figure 14:
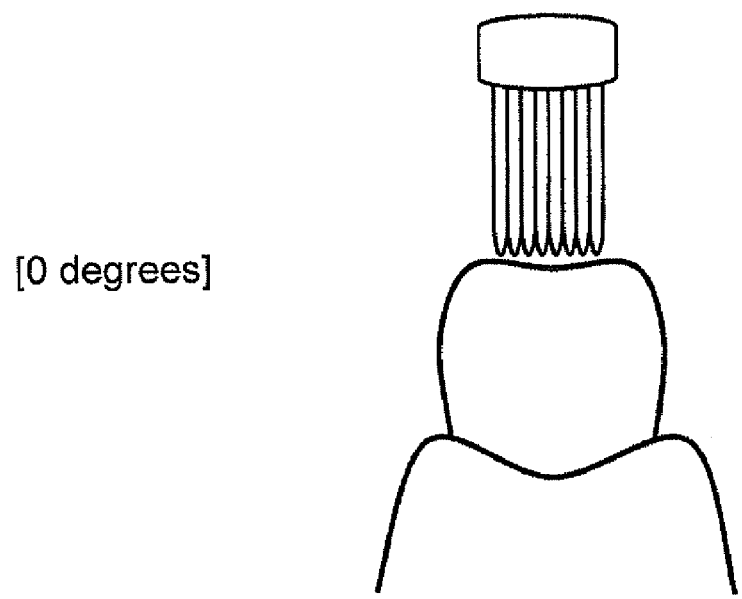
FIG. 14 is a view explaining the brush angle.
Figure 14:
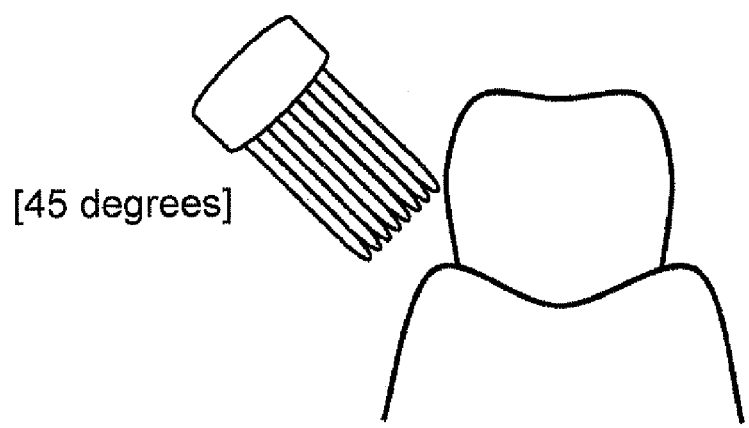
Figure 14:
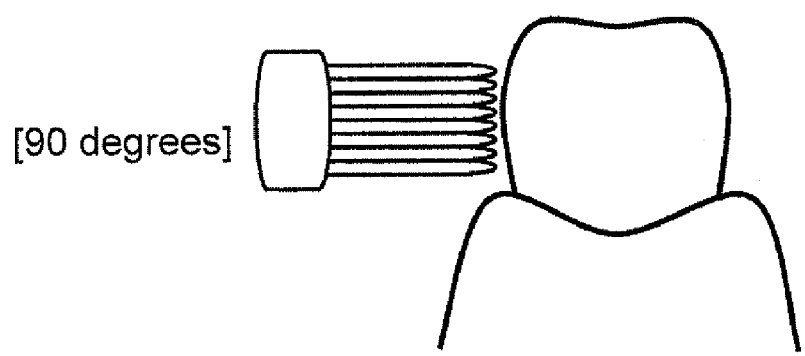

An upper stage of FIG. 14 illustrates a state of the brush angle of 0 degrees, an intermediate stage of FIG. 14 illustrates a state of the brush angle of 45 degrees, and a lower stage of FIG. 14 illustrates a state of the brush angle of 90 degrees. Preferably the brush angle is set to about 0 degrees when the occluding plane is brushed. When the food residue or the dental plaque is effectively scraped out from the periodontal pocket or interdentium, preferably the brush is moved such that the tip of the brush invades into the periodontal pocket or the interdentium, and preferably the brush angle is set to about 45 degrees. On the other hand, when the brush angle is set to 90 degrees, the highest dental plaque removing force is exerted with respect to the tooth plane.

Thus, the optimum brush angle can be fixed depending on the brushing region or a desired cleaning effect. In the first embodiment, the optimum value of the brush angle is set to 0 degrees for the "upper jaw occluding plane" and the "lower jaw occluding plane", the optimum value of the brush angle is set to 45 degrees for the "upper jaw right cheek side", the "upper jaw left tongue side", the "upper jaw left cheek side", the "upper jaw right tongue side", the "lower jaw right cheek side", the "lower jaw left tongue side", the "lower jaw left cheek side", and the "lower jaw right tongue side", and the optimum value of the brush angle is set to 90 degrees for the "upper jaw anterior cheek side", the "upper jaw anterior tongue side", the "lower jaw anterior cheek side", and the "lower jaw anterior tongue side". The setting values are stored in the memory 121. The above-described optimum value of the brush angle is described only by way of example. The optimum value may be set in any way, or preferably the user can change the optimum value to a desired value. Alternatively, a plurality of setting values such as a "dental plaque removing mode" and a "periodontal pocket mode" are previously prepared, the optimum value of "45 degrees" may automatically be set in the brushing region except the occluding plane when the user selects the dental plaque removing mode, and the optimum value of "90 degrees" may automatically be set in the brushing region except the occluding plane when the user selects the periodontal pocket mode.

In S50, the CPU 120 compares the current value of the brush angle obtained in S40 to the optimum value of the brush angle in the brushing region obtained in S30, and the CPU 120 determines whether the brush angle is proper. When the optimum value is defined by one value like the "45 degrees", it is only necessary to evaluate a difference between the current value and the optimum value. When the optimum value is defined by a value region like "40 degrees to 50 degrees", it is only necessary to evaluate whether the current value exists in the value region.

When determining that the brush angle is not proper (NO in S50), the CPU 120 adjusts the brush angle (S60). Specifically, the CPU 120 computes the difference between the optimum value and the current value to send the control signal corresponding to the difference (angle) to the actuator 40, and thereby rotating the brush member 2. Therefore, the orientation of the brush 20 is controlled such that the brush angle becomes the optimum value.

As described above, according to the configuration of the first embodiment, the brush member 2 is automatically rotated according to the attitude of the electric toothbrush to control the brush angle to the optimum value, so that the proper brush angle can easily be realized during the brushing to obtain the good cleaning effect.

Second Embodiment

Figure 15:
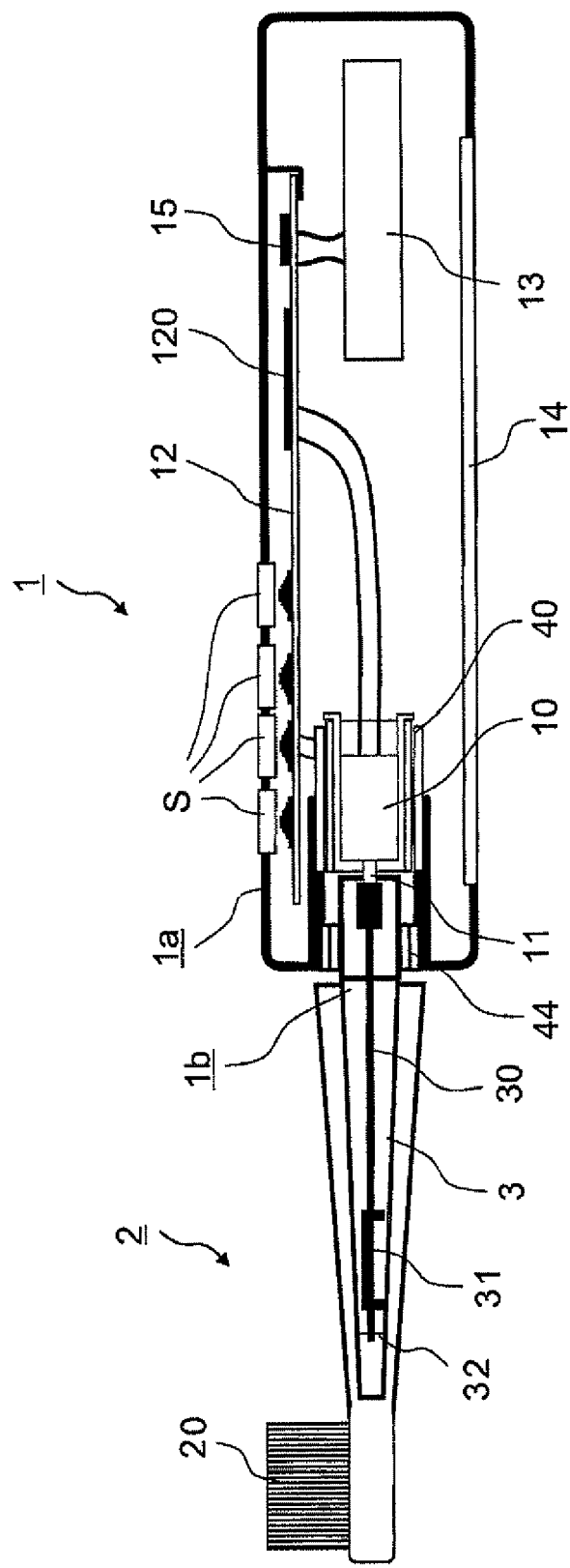
FIG. 15 is a sectional view illustrating an internal configuration of an electric toothbrush according to a second embodiment.

FIG. 15 illustrates a configuration of an electric toothbrush according to a second embodiment of the present invention. The second embodiment differs from the first embodiment in that a bearing 44 is provided between the outer chassis 1a and the inner chassis 1b. With this configuration, position stability of the inner chassis 1b is improved. Because the position of the inner chassis 1b is stabilized, a length in the axis direction of the actuator 40 can be shortened, thereby contributing to miniaturization of the electric toothbrush main body 1.

Third Embodiment

Figure 16:
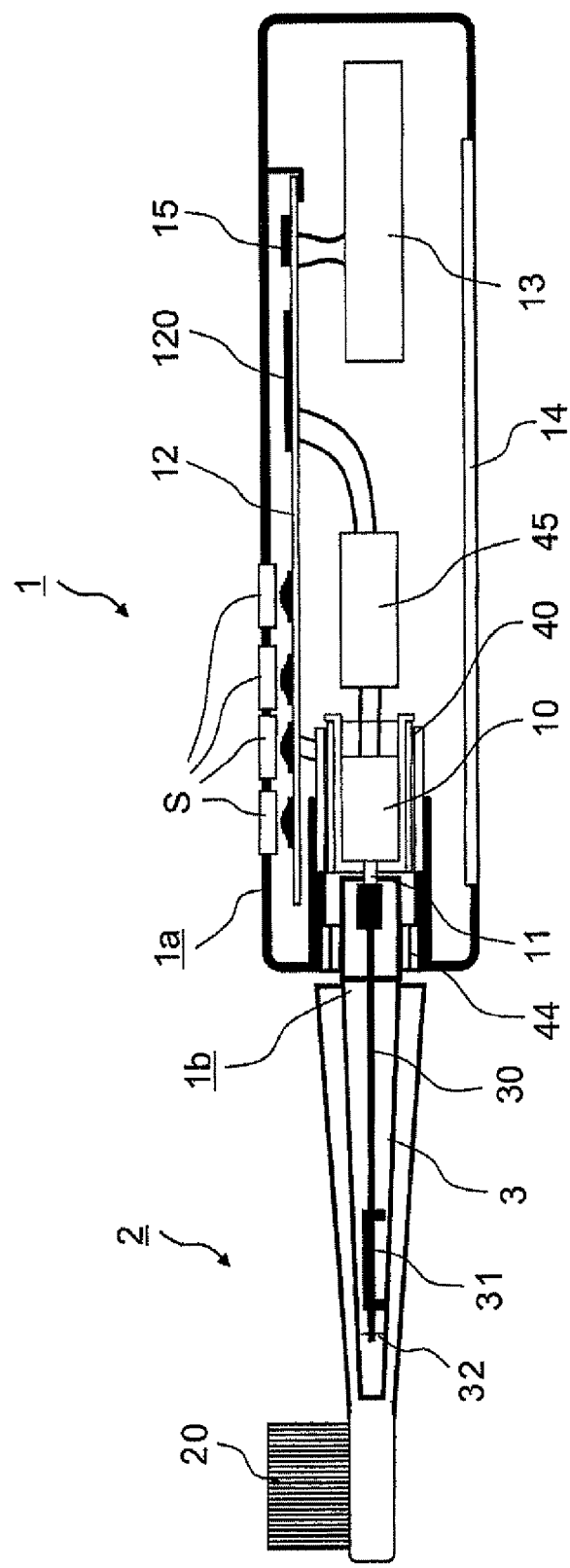
FIG. 16 is a sectional view illustrating an internal configuration of an electric toothbrush according to a third embodiment.

FIG. 16 illustrates a configuration of an electric toothbrush according to a third embodiment of the present invention. In the first and second embodiments, the electric power is supplied to the motor 10 through a lead wire. On the other hand, in the third embodiment, the electric power is supplied to the motor 10 from the driving circuit 12 through an electric connection unit 45.

In the configurations of the first and second embodiments in which the motor 10 and the driving circuit 12 are connected by the lead wire, it is necessary to restrict the rotation range of the actuator 40 in order to prevent the twist or disconnection of the lead wire. On the other hand, the electric connection portion 45 of the third embodiment has a circuit configuration such that the electric connection is secured between the electric power supply line on the driving circuit and an electrode of the motor 10 irrespective of the rotation angle of the actuator 40. For example, the configuration of the third embodiment can preferably be used when the actuator 40 is rotated to 360 degrees or more.

Figure 17:
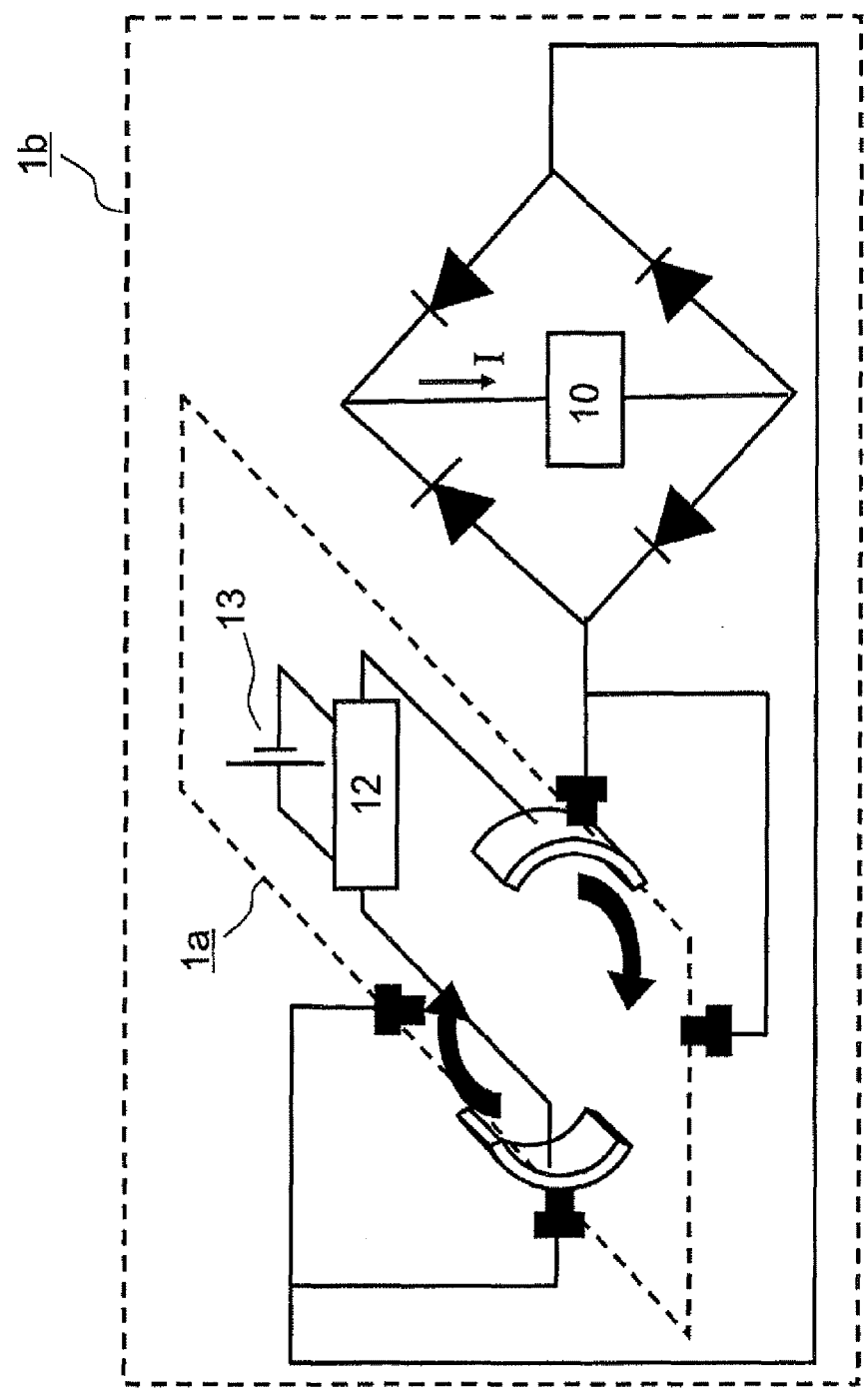
FIG. 17 is a view illustrating a configuration of an electric connection portion using a commutation brush.

FIG. 17 schematically illustrates a circuit configuration using a commutation brush as an example of the electric connection portion 45. In the circuit configuration of FIG. 17, the electric power can be supplied to the motor 10 from the side of the driving circuit 12 irrespective of a contact position of the commutation brush (irrespective of a positional relationship between the inner chassis 1b and the outer chassis 1a) such that a current I in a constant direction is passed through the motor 10.

Figure 18:
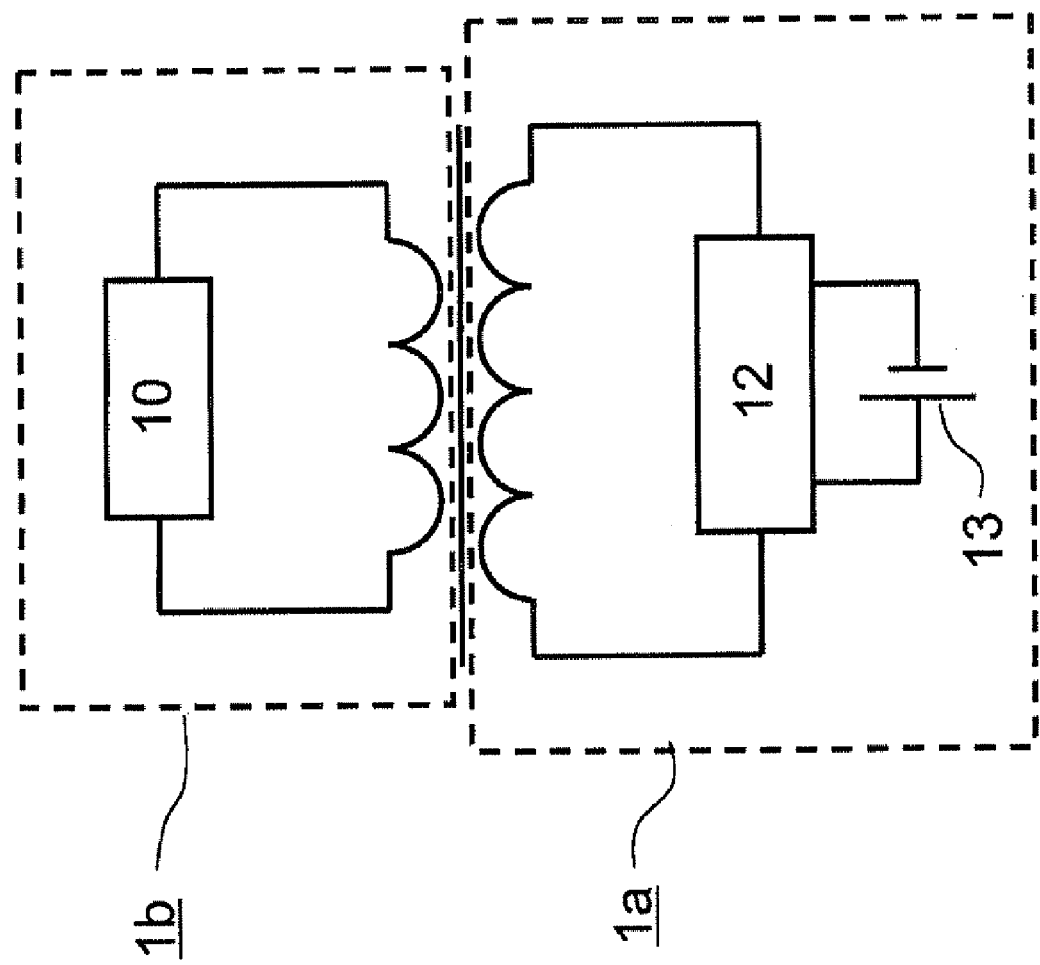
FIG. 18 is a view illustrating a configuration of an electric connection portion using a coil.

FIG. 18 schematically illustrates a circuit configuration using a coil as an example of the electric connection portion 45. In the circuit configuration of FIG. 18, the electrode can be supplied to the motor 10 from the side of the driving circuit 12 by electromagnetic induction.

Fourth Embodiment

A function of informing that the brush angle is the optimum value is provided in the fourth embodiment. Specifically, when the brush angle is determined to be proper in S50 of FIG. 6, the CPU 120 causes a light emitting unit (such as an LED) provided in the outer chassis 1a to emit light. The user can easily recognize that the brush angle is the optimum value by seeing the light emission state of the light emitting unit.

At this point, preferably an informing way (such as a light emission color and a flashing pattern) is changed according to a difference between the current value of the brush angle obtained in S40 and the optimum value of the brushing region obtained in S30. Therefore, the case where the adjustment of the brush angle using the actuator 40 is not required (the attitude of the main body 1 is in the correct state) and the case where the brush angle is adjusted using the actuator 40 (the attitude of the main body 1 is in the incorrect state) are distinguished from each other, so that the user can learn the correct attitude.

For example, sound, vibration, voice and the like can be used as the informing way in addition to the use of the light. For the sound, a volume and a pattern of the sound can be changed according to the difference. For the vibration, strength and a length of the vibration can be changed according to the difference. For the voice, contents such as "Tilt about 30 degrees", "Tilt slightly", and "optimum brush angle" can be informed.

Fifth Embodiment

In a fifth embodiment, a brush motion direction (specifically, the rotating direction of the motor 10), and a motion frequency of the brush (specifically, the number of rotations of the motor 10) are changed according to the detected attitude in addition to the brush angle. In the fifth embodiment, other configurations are similar to those of the embodiments.

Therefore, a characteristic configuration of the fifth embodiment will mainly be described below.

(Vibration Characteristic)

In the electric toothbrush, as described above, the vibration of the brush is generated by utilizing a gyrating motion of the eccentric shaft, and the brush 20 is vibrated in the plane perpendicular to the rotating axis of the motor 10 while drawing an ellipsoidal orbit. The inventors observe and analyze the vibration of the brush while the number of vibrations (the number of rotations of the motor) is changed, and the inventors find that the electric toothbrush has the following vibration characteristic.

(1) The brush portion has at least two resonant points (resonant frequencies).

Figure 19:
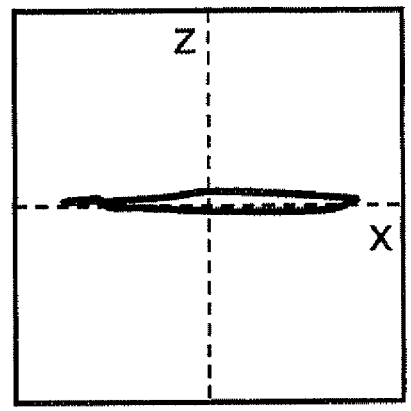
FIG. 19 is a view explaining a trajectory of a brush.
Figure 19:
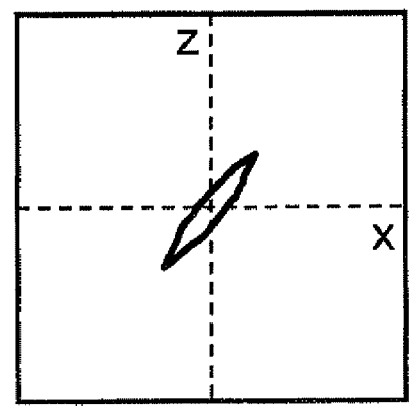
Figure 19:
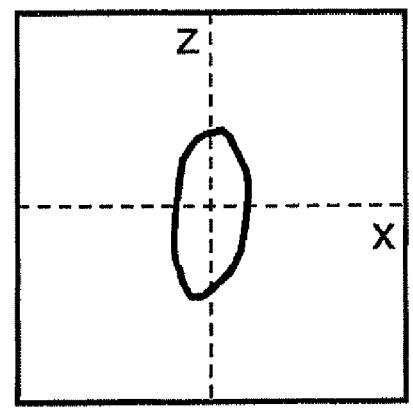

(2) Resonant directions differ from each other at each resonant point, Specifically, as illustrated in FIG. 19, amplitude in the x-axis direction parallel to the brush surface is increased at the resonant point (first resonance: about 12500 spm) on the side of the low number of vibrations. The amplitude in the z-axis direction perpendicular to the brush surface is increased at the resonant point (second resonance: about 38000 spm) on the side of the low number of vibrations. The brush draws an orbit (about 45 degrees) oblique to the x-axis (z-axis) out of the resonance (for example, about 26500 spm). At this point, "spm" is a unit expressing the number of swing times per minute.

The reason the plurality of resonant points having the different directions emerge is attributed to the fact that the resonant points largely depend on the structure or driving principle of the electric toothbrush. The inventors repeatedly perform the experiments while the configurations of the eccentric shaft and brush are changed, and the inventors obtain the knowledge that the first resonant point is a characteristic depending mainly on the motion transmission mechanism while the second resonant point is a characteristic depending mainly on the brush. In other words, it is found that the number of vibrations and the amplitude of the first resonant point can be adjusted by changing a structure or a shape (briefly, for example, the position, size, and weight of the weight of the eccentric shaft) of the motion transmission mechanism, and it is found that the number of vibrations and the amplitude of the second resonant point can be adjusted by changing the structure or shape of the brush.

Figure 20:
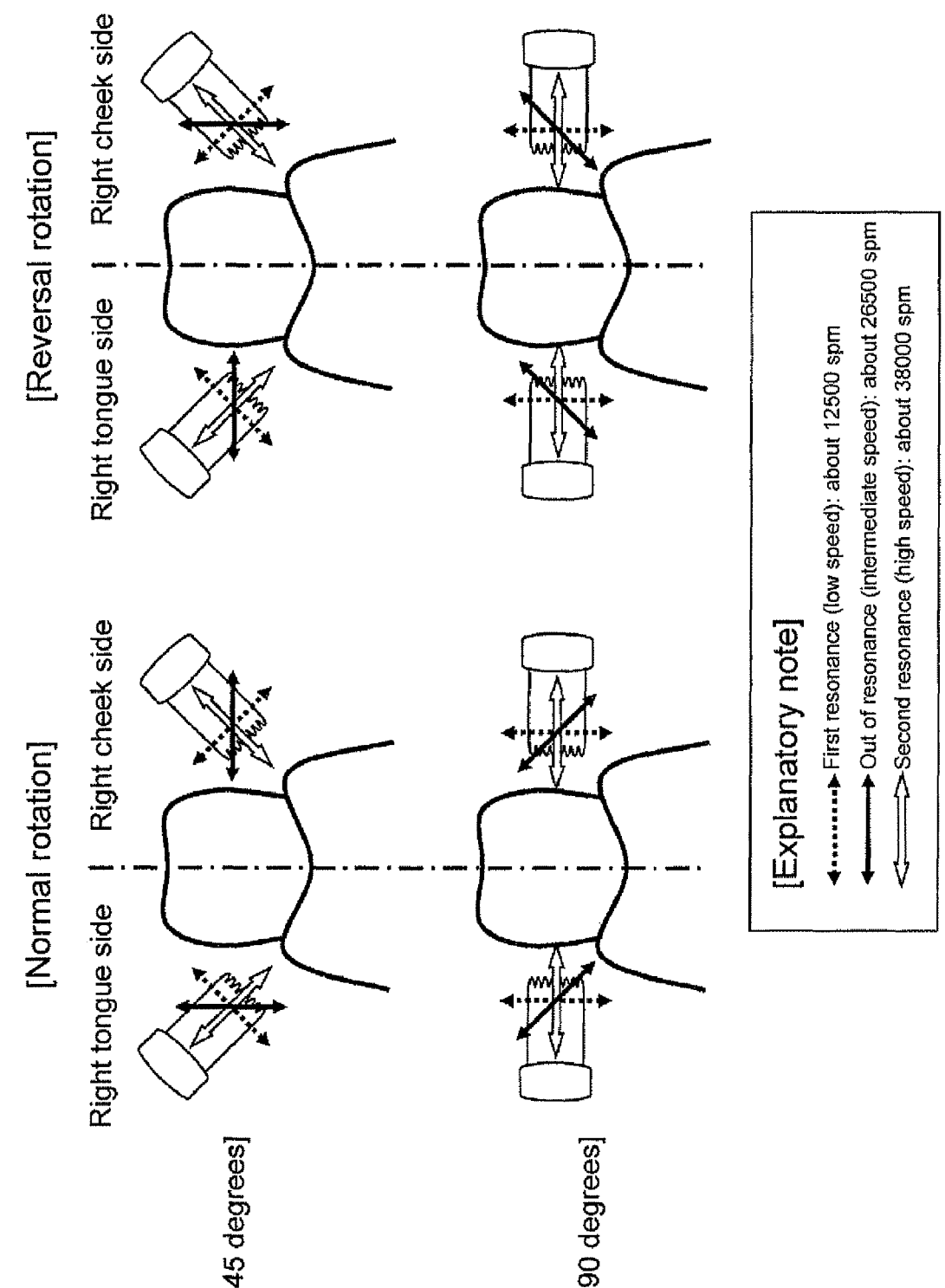
FIG. 20 is a view illustrating a relationship between the brush angle and brush motion.

The upper stage of FIG. 20 illustrates the state of the brush angle of 45 degrees, and the lower stage of FIG. 20 illustrates the state of the brush angle of 90 degrees. The left of FIG. 20 illustrates the state of the normal rotation of the motor, and the right of FIG. 20 illustrates the state of the reversal rotation of the motor. Each arrow indicates the motion of the brush (the direction of the largest amplitude). Roughly, the brush is horizontally moved (x-axis direction) in the first resonance, the brush is vertically moved (z-axis direction) in the second resonance, and the brush is obliquely moved out of the resonance.

When the food residue or the dental plaque is effectively scraped out from the periodontal pocket or interdentium, preferably the brush is moved such that the tip of the brush invades into the periodontal pocket or the interdentium. That is, preferably the brush moving direction is oblique to the tooth axis (for example, 45 degrees). Accordingly, as can be seen from an example of FIG. 20, the motion of the second resonance is optimum for the brush angle of 45 degrees. On the other hand, for the brush angle of 90 degrees, the motion out of the resonance of the normal rotation of the motor is optimum on the lower jaw right tongue side, and the motion out of the resonance of the reversal rotation of the motor is optimum on the lower jaw right cheek side. According to the similar idea, the optimum operating mode (the rotating direction of the motor and the number of vibrations of the brush) can be determined for each combination of the brushing region and the brush angle.

Figure 21:
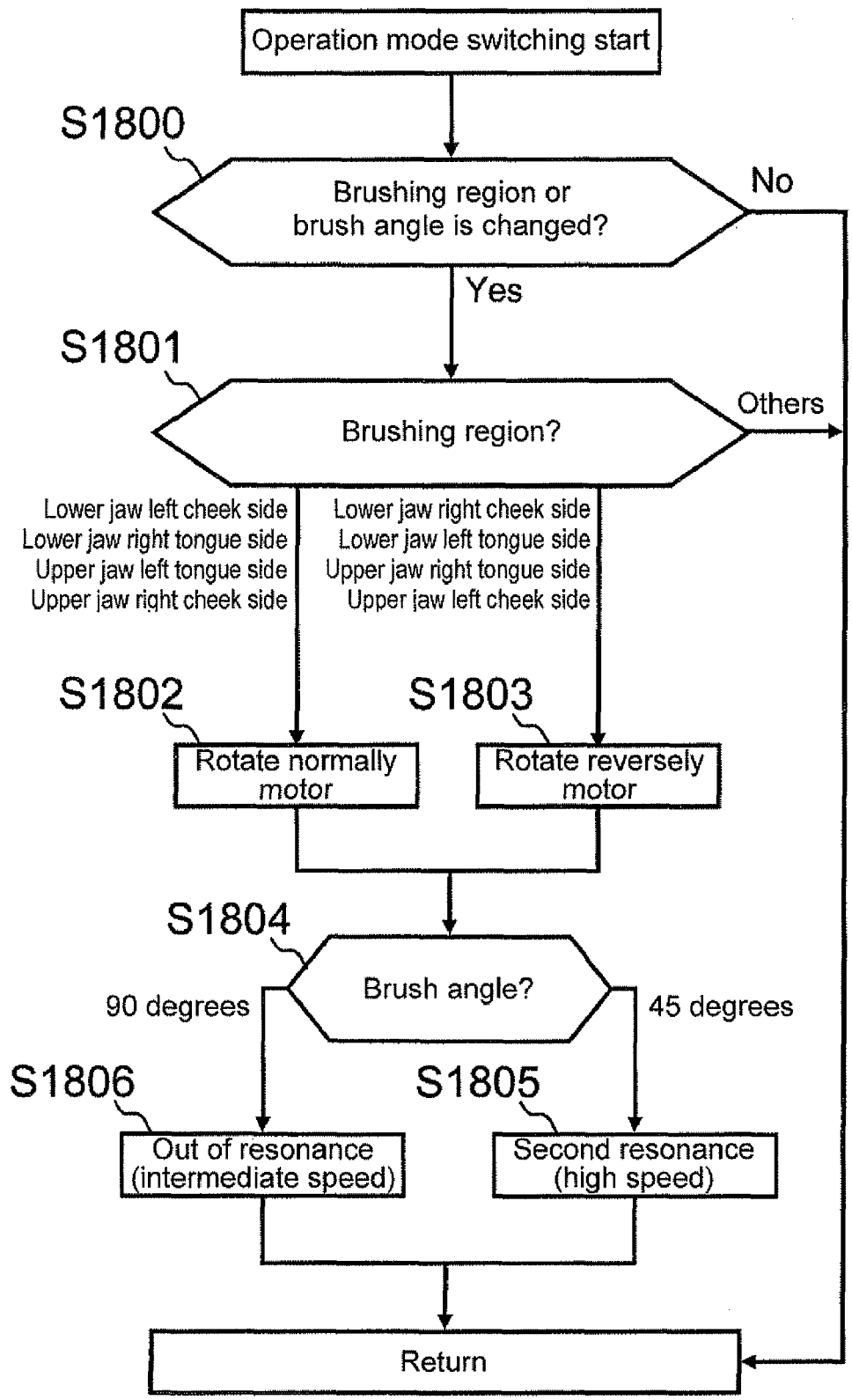
FIG. 21 is a flowchart of operation mode switching processing according to a fifth embodiment.

FIG. 21 is a flowchart of operation mode switching processing of the fifth embodiment. For example, the operation mode switching processing is performed after S60 of FIG. 6.

The CPU 120 compares the brushing region obtained in S30 and the brush angle (or the optimum value of the brush angle) obtained in S40 to the brushing region and brush angle of the previous processing to check whether the brushing region or the brush angle is changed (S1800). The brushing region and brush angle of the previous processing are stored in the memory.

When the brushing region or the brush angle is changed (YES in S1800), the CPU 120 determines to which a first group of "lower jaw left cheek side, lower jaw right tongue side, upper jaw left tongue side, and upper jaw right cheek side" or a second group of "lower jaw right cheek side, lower jaw left tongue side, upper jaw right tongue side, and upper jaw left cheek side" the current brushing region corresponds (S1801). When the current brushing region corresponds to the first group, the CPU 120 normally rotates the motor (S1802). When the current brushing region corresponds to the second group, the CPU 120 reversely rotates the motor (S1803). The CPU 12 controls the number of vibrations of the brush at the second resonance (high speed) when the brush angle is 45 degrees (S1804 and S1805), and the CPU 12 controls the number of vibrations of the brush out of the resonance (intermediate speed) when the brush angle is 90 degrees (S1806).

As described above, according to the control of the fifth embodiment, based on the pieces of information on the brushing region and the brush angle, the motion of the tip of the brush most suitable to the brushing of the interdentium or periodontal pocket can be realized to further enhance the dental plaque removing force.

In the fifth embodiment, both the brush motion direction and the brush motion frequency are controlled. Alternatively, preferably one of the brush motion direction and the brush motion frequency is controlled. For example, the motion frequency is decreased to weaken the brushing strength for the region where a gum is sensitive, and the motion frequency is increased to strengthen the brushing strength for the region where the high cleaning effect is desired. Therefore, the improvement of the cleaning effect and a medical treatment feeling can be achieved. Because the vibrating mechanism of the toothbrush is symmetrical in relation to the yz-plane, the brush draws a symmetrical orbit in relation to the yz-plane when the rotating direction of the motor is reversed. Therefore, the rotating direction of the motor is changed according to the brushing region such that the tip of the brush is moved in the direction in which the dental plaque is scraped out from the periodontal pocket.

Sixth Embodiment

In a configuration according to a sixth embodiment, the brushing region and the brush angle are estimated with a uniaxial acceleration sensor.

Figure 22:
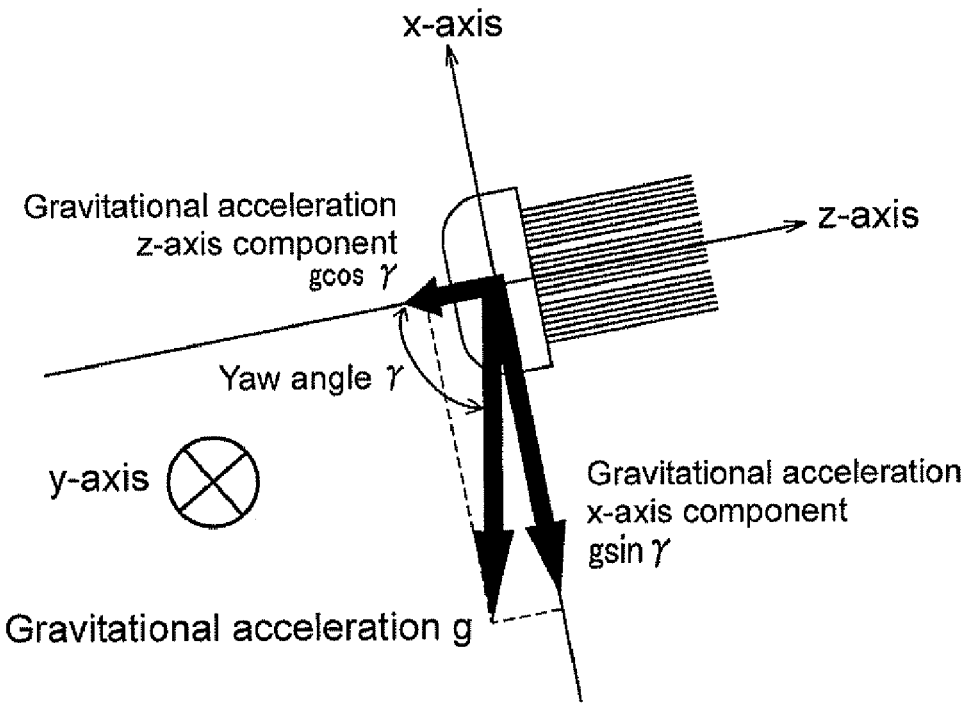
FIG. 22 is a view explaining attitude detection according to a sixth embodiment.
Figure 22:
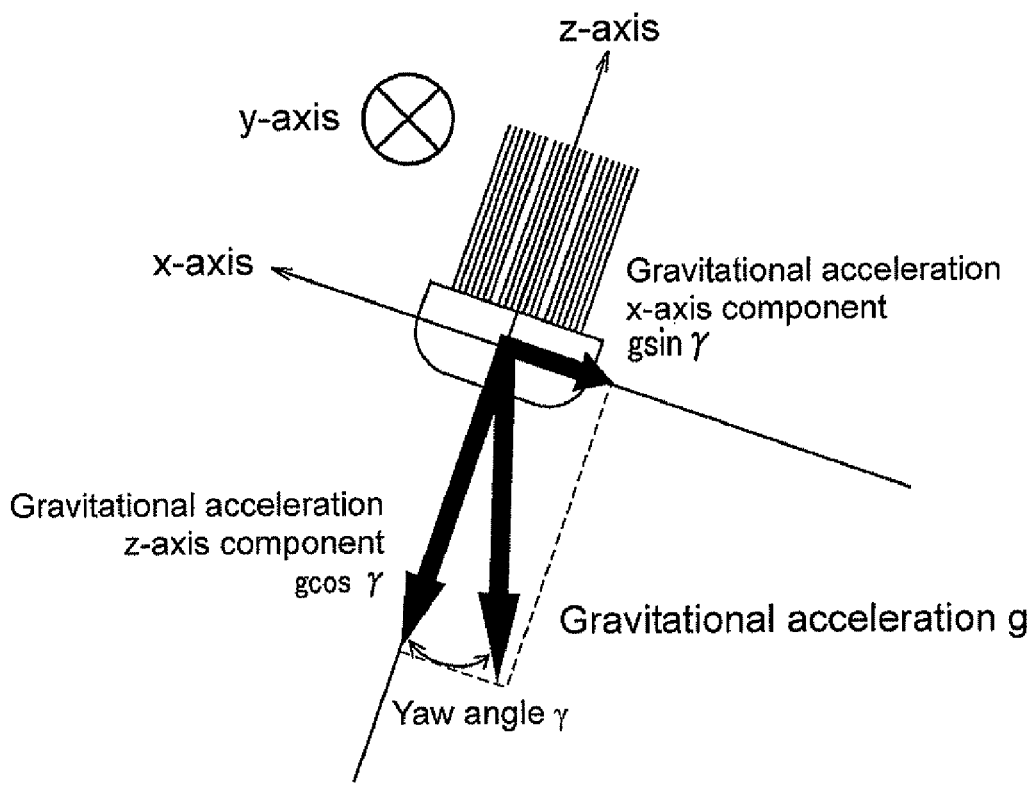

An upper stage of FIG. 22 illustrates a state in which the tooth plane on the cheek side or tongue side is brushed. At this point, the brush angle (yaw angle γ) becomes about 90 degrees, the component in the x-axis direction of the gravitational acceleration becomes about 1 g or −1 g (the positive and negative signs correspond to the right and left of the tooth row), and the component in the z-axis direction of the gravitational acceleration becomes substantial zero. On the other hand, the lower stage of FIG. 22 illustrates the state in which the occluding plane is brushed. At this point, the brush angle (yaw angle γ) becomes substantial zero, the component in the x-axis direction of the gravitational acceleration becomes substantial zero, and the component in the z-axis direction of the gravitational acceleration becomes about 1 g or −1 g (the positive and negative signs correspond to the right and left of the tooth row).

When the above-described characteristic is utilized, the determination whether the brushing region is the "tooth plane on the cheek side or tongue side" or the "occluding plane" and the determination of the up and down or the right or left can be made only with the x-axis acceleration sensor or the z-axis acceleration sensor. Similarly to the embodiments, the brush angle can be computed from the output of the x-axis or z-axis acceleration sensor. The pieces processing are similar to those of the embodiments after the brushing region and the brush angle are estimated.

Seventh Embodiment

An electric toothbrush according to a seventh embodiment has an automatic returning function of returning the brush member to an initial position after use of the electric toothbrush. Other configurations are similar to those of the embodiments.

Figure 23:
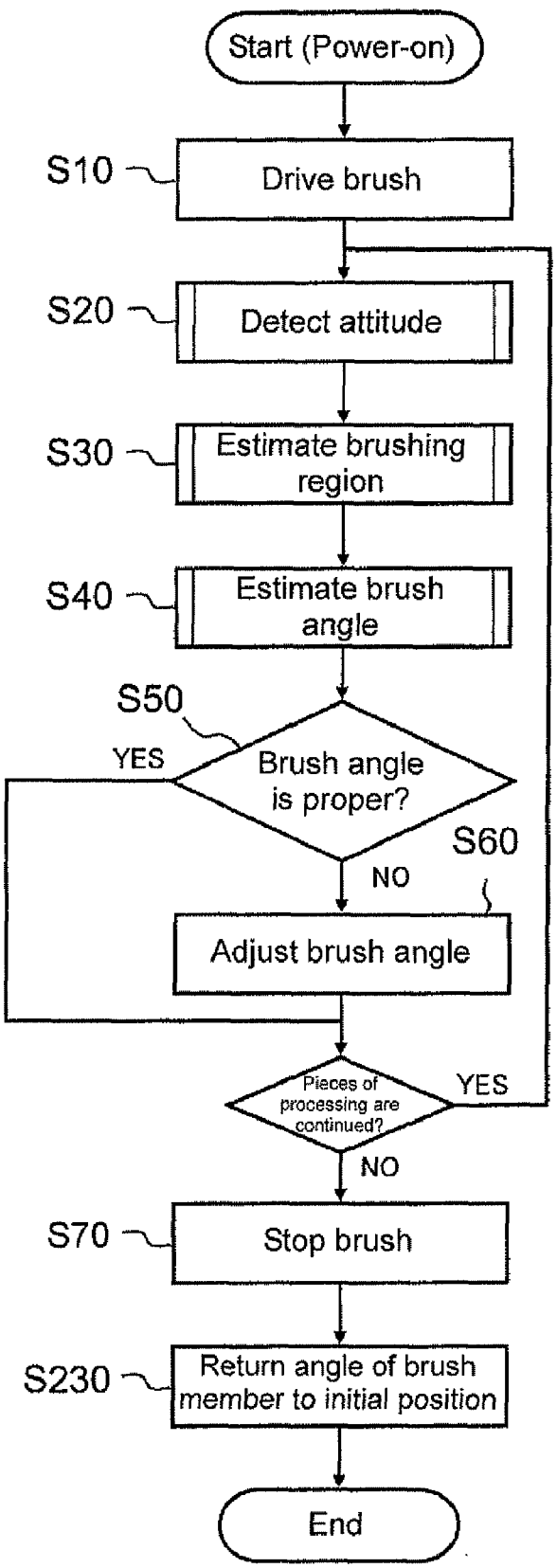
FIG. 23 is a view explaining automatic return processing according to a seventh embodiment.

As illustrated in a flowchart of FIG. 23, when the electric toothbrush is powered off by a switch manipulation, or when the continuous operation time measured by the timer reaches the predetermined time (for example, two minutes), the loop of S20 to S60 is ended (pieces of processing are continued?: NO), and the drive of the brush is stopped (S70). Then, in S230, the CPU 120 controls the actuator 40 to return the angle of the brush member 2 (the orientation of the brush) to the initial position (home position). In the seventh embodiment, the state in which the brush surface is oriented toward the same side as the switch S of the electric toothbrush main body (see FIG. 2) is defined as the initial position.

According to the automatic returning function of the seventh embodiment, even if the brushing of teeth is ended while the brush orientation is deviated from the initial position, the brush orientation is automatically returned to the initial position until the next brushing of teeth is started. Therefore, the brush angle can quickly reach the optimum value when the next brushing of teeth is started.

Preferably the control is performed such that the brush member is returned to the initial position by detecting that the electric toothbrush is placed on the charger 100. In consideration of the restart of the brushing of teeth immediately after the power-off or the automatic stop with the timer, preferably the brush member is returned to the initial position after a predetermined time (for example, one minute) elapses since the power-off is detected.

In the seventh embodiment, the automatic return processing is performed after the use of the electric toothbrush is ended. However, the similar effect is obtained even if the automatic return processing is performed when the use of the electric toothbrush is started (for example, when the electric toothbrush is power-on, or when the electric toothbrush is detached from the charger 100).

<Others>

The configurations of the embodiments of the present invention are described only by way of example. The scope of the present invention is not limited to the embodiments, but various modifications can be made without departing from the scope of the technical idea of the present invention. For example, the configurations of the embodiments are preferably combined. In the embodiments, the electric toothbrush has the vibration method in which the eccentric weight is used by way of example. However, the present invention can be applied to an electric toothbrush in which another motion method is adopted. For example, the present invention can be applied to electric toothbrushes in which rotation-reciprocating motion, linear reciprocating motion, rotation motion of bristles of brush, and a combination thereof that can be switched are adopted. The present invention can be applied to not the rechargeable type electric toothbrush, but a battery type electric toothbrush and a type of electric toothbrush in which a power cord is connected.

In order to further enhance detection accuracy of the brush attitude and estimation accuracy of the brushing region or brush angle, preferably a moving amount of the brush with respect to a reference position and a relative attitude are computed from the output of the acceleration sensor and a gyroscope. As to the reference position, the attitude at the point of the power-on may be set to the reference position, or a mechanism (for example, the user presses the switch while holding horizontally the toothbrush main body to abut the brush on the upper jaw anterior cheek side) in which the user inputs the reference position (the start position of the brushing) may be provided. The moving amount (moving distance) can be computed by second order differential of the dynamic acceleration component in each of the x-axis direction, y-axis direction, and z-axis direction, which are obtained from the acceleration sensor output. However, in computing the moving amount, a coordinate system xyz of the toothbrush is converted into a coordinate system XYZ in which the direction of the gravitational acceleration is set to Z-axis (preferably the reference position is set to an origin). For example, each moving distance of X, Y, Z is computed and accumulated in each clock to be able to determine a relative position with respect to the reference position (initial position). When the relative position with respect to the reference position is determined, the brushing region can be identified more correctly and in more detail than the embodiments. Preferably the brush position is computed by utilizing orientation information obtained from a magnetic sensor and the like. A bandpass filter such as high pass filter can be used when the dynamic acceleration component is extracted from the acceleration sensor output. At this point, preferably a frequency component of about 100 Hz to about 300 Hz corresponding to the brush driving frequency is cut in order to remove a noise caused by the brush vibration. Preferably the moving amount and moving direction are more correctly computed by the combination with the gyroscope. As to the anterior tooth, because the brush attitude turns 180 degrees around according to by which the right or left hand the toothbrush main body is held, the user registers a dominant hand (the hand by which the tooth brush is held), and the determination algorithm for the brushing region or the operation mode (the motor rotating direction and the brush motion) may be changed according to the registered dominant hand.

A mouth cavity is imaged with a compact camera provided in the leading end portion of the brush member 2, and the image information may be utilized in detecting the brush attitude. A temperature sensor or an optical sensor is provided in the leading end portion of the brush member 2, and the detection result can be utilized in detecting the brush attitude.

The invention claimed is:

1. An electric toothbrush comprising:
an electric toothbrush main body that includes a grip portion;
a brush member that includes a brush;
driving means for moving the brush;
rotation means for relatively rotating the brush member with respect to the electric toothbrush main body in order to change an orientation of the brush;
attitude detection means for detecting an attitude of the electric toothbrush main body; and
control means for controlling the rotation means such that a brush angle that is of an angle of the brush with respect to a tooth axis becomes a predetermined optimum value based on the detected attitude.

2. The electric toothbrush according to claim 1, wherein the control means includes:
region estimation means for estimating a currently-brushed brushing region in a plurality of regions defined by classifying a surface of a tooth row based on the detected attitude; and
brush angle estimation means for estimating the brush angle that is of the angle of the brush with respect to the tooth axis based on the detected attitude, and
the optimum value of the brush angle previously set in each brushing region and the estimated brush angle are compared to control the rotation means such that the brush angle becomes the optimum value.

3. The electric toothbrush according to claim 2, wherein the control means controls the driving means such that a motion direction or a motion frequency of the brush is changed according to the detected attitude.

4. The electric toothbrush according to claim 2, wherein the attitude detection means detects the attitude based on an output of an acceleration sensor.

5. The electric toothbrush according to claim 2, further comprising informing means for informing that the brush angle is the optimum value.

6. The electric toothbrush according to claim 2, wherein the optimum value is changeable.

7. The electric toothbrush according to claim 2, wherein the control means controls the rotation means such that the brush member is located at a predetermined initial position after the electric toothbrush is used or when use of the electric toothbrush is started.

8. The electric toothbrush according to claim 1, wherein the control means controls the driving means such that a motion direction or a motion frequency of the brush is changed according to the detected attitude.

9. The electric toothbrush according to claim 1, wherein the attitude detection means detects the attitude based on an output of an acceleration sensor.

10. The electric toothbrush according to claim 1, further comprising informing means for informing that the brush angle is the optimum value.

11. The electric toothbrush according to claim 1, wherein the optimum value is changeable.

12. The electric toothbrush according to claim 1, wherein the control means controls the rotation means such that the brush member is located at a predetermined initial position after the electric toothbrush is used or when use of the electric toothbrush is started.

* * * * *